United States Patent [19]

Desobry

[11] Patent Number: 5,340,701
[45] Date of Patent: Aug. 23, 1994

[54] FLUORINE-FREE TITANOCENES AND THE USE THEREOF

[75] Inventor: Vincent Desobry, Marly, Switzerland

[73] Assignee: Ciba-Geigy Corporation, Ardsley, N.Y.

[21] Appl. No.: 43,237

[22] Filed: Apr. 6, 1993

[30] Foreign Application Priority Data

Apr. 9, 1992 [CH] Switzerland ............. 1155/92-0

[51] Int. Cl.$^5$ .................. G03C 5/00; C07F 15/02; C07F 7/28
[52] U.S. Cl. .................. 430/325; 430/270; 430/280; 430/281; 430/286; 430/288; 522/65; 522/66; 556/53; 544/64; 544/225
[58] Field of Search ............. 430/325, 270, 280, 281, 430/286, 288; 522/65, 66; 556/53; 544/64, 225

[56] References Cited

U.S. PATENT DOCUMENTS

| | | | |
|---|---|---|---|
| 4,548,891 | 10/1985 | Riediker et al. | 430/283 |
| 4,590,287 | 5/1986 | Riediker et al. | 556/53 |
| 4,713,401 | 12/1987 | Riediker et al. | 522/65 |
| 4,855,468 | 8/1989 | Riediker et al. | 556/53 |
| 4,910,121 | 3/1990 | Riediker et al. | 430/281 |
| 4,963,470 | 10/1990 | Klingert et al. | 430/281 |
| 4,973,722 | 11/1990 | Doggweiler et al. | 556/53 |
| 5,008,302 | 4/1991 | Hüsler et al. | 522/14 |
| 5,026,625 | 6/1991 | Riediker et al. | 430/281 |
| 5,068,371 | 11/1991 | Steiner et al. | 556/53 |
| 5,192,642 | 3/1993 | Steiner et al. | 430/281 |

OTHER PUBLICATIONS

J. Am. Chem. Soc. 77, 3604 (1959).
J. Organomet. Chem. 2 (1964), 206–212.
J. Organomet. Chem. 358 (1988), 525.

Primary Examiner—Marion E. McCamish
Assistant Examiner—Mark A. Chapman
Attorney, Agent, or Firm—Luther A. R. Hall

[57] ABSTRACT

Fluorine-free titanocene compounds of the formula I or II

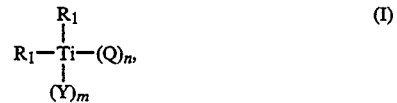

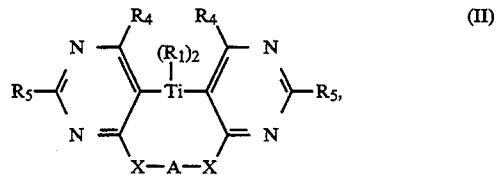

in which both $R_1$ radicals are preferably, independently of one another, cyclopentadienyl$^\ominus$, which is unsubstituted or substituted by alkyl, alkoxy or —Si(R$_2$)$_3$, and both $R_2$ radicals are, in particular, alkyl,

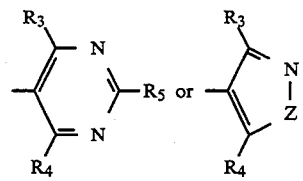

Z is —NR$_{10}$—, —O— or —S—,
Y is Cl, Br, I, CN, SCN, —O—CO—CH$_3$, —O—CO—phenyl or —O—SO$_2$—CH$_3$,
n is 1 or 2,
m is 0 or 1, where the sum of n and m must be 2,
R$_3$, R$_4$ and R$_5$ are in particular, independently of one another, hydrogen, Cl, alkyl, cycloalkyl, adamantyl, phenyl, pyrryl or biphenylyl, where these radicals are unsubstituted or substituted by alkyl, Cl, alkylthio, —NR$_8$R$_9$, phenyl, phenylthio or C$_1$–C$_{10}$alkoxy, or R$_3$, R$_4$ and R$_5$ are alkenyl, alkoxy, cycloalkoxy, phenoxy, benzyloxy, tetrahydrofurfuryloxy, alkylthio, cycloalkylthio, benzylthio or phenylthio, where R$_3$ and R$_4$ are not simultaneously hydrogen, and
if Q is a pyrimidyl radical, at least one radical R$_3$ or R$_4$ is alkoxy, cycloalkoxy, phenoxy, benzyloxy, tetrahydrofurfuryloxy or alkenyloxy, and
if Z is —NR$_{10}$—, R$_3$ and R$_4$ are Cl Br or I, both radicals $R_6$, independently of one another, are alkyl or alkenyl or both radicals $R_6$ together with the nitrogen atom to which they are bonded, form a morpholino radical, $R_7$ is alkyl, cycloalkyl or phenyl, $R_8$ is phenyl or α-tertiary $C_4$–$C_6$alkyl, $R_9$ is, in particular, hydrogen, alkyl, cycloalkyl, phenyl or a

radical, where, in addition, the two $R_9$ radicals in $-N(R_9)_2$ are identical or different and, together with the nitrogen atom to which they are bonded, may form a 5- or 6-membered heterocyclic ring which, in addition to the nitrogen atom, may also contain further nitrogen, oxygen or sulfur atoms, $R_{10}$ is as defined for $R_9$ or additionally, in particular, is phenyl which is unsubstituted or substituted by Cl, $C_1$–$C_{12}$alkyl, $C_1$–$C_{10}$alkoxy, $C_1$–$C_8$alkylthio, phenylthio, morpholino or $-N(C_1$–$C_4$alkyl$)_2$, X is $-O-$, $-S-$,

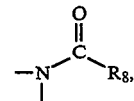

methylene or ethylene, and

A is $C_1$–$C_{12}$alkylene or $-X-A-X-$ is a direct bond, are suitable as photoinitiators for photopolymerisation of compounds containing ethylenically unsaturated double bonds.

23 Claims, No Drawings

FLUORINE-FREE TITANOCENES AND THE USE THEREOF

The invention relates to novel, fluorine-free titanocenes, to the use thereof as photoinitiators, and to compositions which contain these titanocenes.

Titanocene compounds are known as highly effective photoinitiators. U.S. Pat. Nos. 4,590,287 and 4,910,121 describe, for example, titanocenes as photoinitiators which are substituted on the aromatic ring by halogen, alkyl or amino radicals. U.S. Pat. No. 4,548,891 discloses the use of these compounds as photoinitiators for the production of relief plates. U.S. Pat. Nos. 4,713,401 and 4,855,468 disclose titanocene compounds which are substituted on the aromatic radicals by at least one trifluoromethyl group. U.S. Pat. No. 4,963,470 discloses titanocenes which are substituted on the cyclopentadienyl ring by trialkylsilicon radicals. Titanocene compounds containing nitrogen substituents and heterocyclic substituents on the aromatic ring are disclosed in U.S. Pat. Nos. 5,008,302, 5,026,625 and 5,068,371. U.S. Pat. No. 5,192,642 describes titanocenes which carry ester substituents on the aromatic radical. The titanocene compounds described in the above prior art which are effective as photoinitiators have one thing in common: the aromatic ligands on the titanium atom are substituted by fluorine or trifluoromethyl groups in at least one ortho-position to the carbon atom bonded to the titanium. L. Summers, R. H. Uloth and A. Holmers, J. Am. Chem. Soc. 77, 3604 (1959), note that bis(alkylaryl)bis(cyclopentadienyl)titanium compounds have only low stability. M. A. Chaudari, P. M. Treichel and F. G. A. Stone compare the stability of titanocenes having perfluorinated aryl ligands with the corresponding halogen-free titanocenes (J. Organomet. Chem. 2, 206-212 (1964)). The titanocenes containing the perfluorinated aromatic radicals prove to be significantly more stable. The same result is obtained in the investigations by R. Usón, J. Fornids and M. Tomás, J. Organomet. Chem. 358, 525–543 (1988), where the fluorine substitution in the ortho-position plays an important role.

The handling, preparation and disposal of fluorine-containing compounds is frequently not simple to achieve in industry. There is therefore a demand for titanocenes which can be used as photoinitiators, but contain no fluorine atoms.

It has now been found, surprisingly, that titanocene compounds containing pyrimidine ligands are stable, even without substitution by fluorine, and are effective photoinitiators.

The invention therefore relates to compounds of the formulae I and II

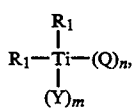

(I)

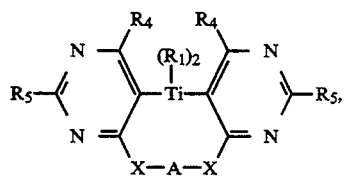

(II)

in which both $R_1$ radicals are, independently of one another, cyclopentadienyl$^\ominus$, indenyl$^\ominus$ or 4,5,6,7-tetrahydroindenyl$^\ominus$, these radicals being unsubstituted or substituted by $C_1$-$C_{18}$alkyl, $C_1$-$C_{18}$alkoxy, $C_2$-$C_{18}$alkenyl, $C_5$-$C_8$cycloalkyl, $C_1$-$C_4$alkyl-$C_5$-$C_8$cycloalkyl, phenyl, naphthyl, phenyl-substituted $C_1$-$C_{12}$alkyl, —Si(R$_2$)$_3$, —Ge(R$_2$)$_3$, cyano, Cl Br or I, and the two $R_2$ radicals, independently of one another, are $C_1$-$C_{12}$alkyl, $C_5$-$C_8$cycloalkyl, or unsubstituted or $C_1$-$C_6$alkyl-substituted phenyl or benzyl, Q is a

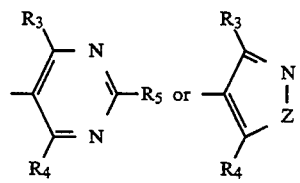

radical,

Z is —NR$_{10}$—, —O— or —S—,

Y is Cl Br, I, CN, SCN, —O—CO—CH$_3$, —O—CO—phenyl or —O—SO$_2$—CH$_3$, n is 1 or 2, m is 0 or 1, where the sum of n and m must be 2, $R_3$, $R_4$ and $R_5$, independently of one another, are hydrogen, Cl, Br, I, unsubstituted or $C_1$-$C_4$alkoxy-, $C_5$-$C_6$cycloalkyl- or phenyl-substituted $C_1$-$C_{12}$alkyl, unsubstituted or $C_1$-$C_4$alkyl-substituted $C_3$-$C_8$cycloalkyl or adamantyl, or $R_3$, $R_4$ and $R_5$ are phenyl, pyrryl, furyl, thienyl, imidazolyl, pyridyl, naphthyl, anthryl, phenanthryl or biphenylyl where the radicals phenyl, pyrryl, furyl, thienyl, imidazolyl, pyridyl, naphthyl, anthryl, phenanthryl or biphenylyl are unsubstituted or substituted by $C_1$-$C_{12}$alkyl, cyclopentyl, cyclohexyl, Cl, Br, I, $C_1$-$C_8$alkylthio, —NR$_8$R$_9$, phenyl, phenylthio or-/and $C_1$-$C_{10}$alkoxy, or $R_3$, $R_4$ and $R_5$ are unsubstituted $C_2$-$C_{12}$alkenyl or $C_2$-$C_{12}$alkenyl which is substituted by unsubstituted or $C_1$-$C_4$alkyl-, $C_1$-$C_4$alkoxy-, $C_1$-$C_4$alkylthio-, Cl-, Br- or I-substituted phenyl or

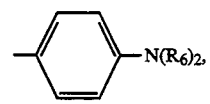

or $R_3$, $R_4$ and $R_5$ are unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy, $C_2$-$C_6$alkenyloxy, —O—Si—(R$_7$)$_3$, $C_1$-$C_8$alkylthio, $C_3$-$C_8$cycloalkylthio, unsubstituted or $C_1$-$C_4$alkyl- and/or $C_1$-$C_4$alkoxy-substituted benzylthio, unsubstituted or $C_1$-$C_4$alkyl- and/or $C_1$-$C_4$alkoxy-substituted phenylthio, —S(O)R$_8$, —SO$_2$R$_8$, —N(R$_9$)$_2$,

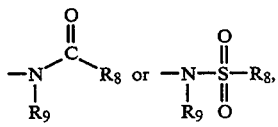

where $R_3$ and $R_4$ are not simultaneously hydrogen, and at least one radical $R_3$ or $R_4$ in the

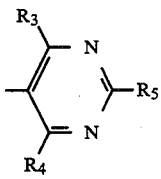

radical is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy, and in the case where Z is —$NR_{10}$—, $R_3$ and $R_4$ are Cl, Br or I, the two $R_6$ radicals, independently of one another, are $C_1$-$C_4$alkyl or $C_2$-$C_{10}$alkenyl, or the two $R_6$ radicals, together with the nitrogen atom to which they are bonded, form a morpholino radical, $R_7$ is $C_1$-$C_{12}$alkyl, $C_5$-$C_8$cycloalkyl or unsubstituted or $C_1$-$C_6$alkyl-substituted phenyl, $R_8$ is unsubstituted or $C_1$-$C_4$alkyl-substituted phenyl or α-tertiary $C_4$-$C_6$alkyl, $R_9$ is unsubstituted or phenyl-, $C_7$-$C_{12}$alkylphenyl-, $C_5$-$C_8$cycloalkyl- or $C_1$-$C_4$alkyl-$C_5$-$C_8$cycloalkyl-substituted $C_1$-$C_8$alkyl, $C_2$-$C_8$alkenyl, unsubstituted or $C_1$-$C_4$alkyl-substituted $C_5$-$C_8$cycloalkyl, $C_6$-$C_{20}$cycloalkenylalkyl, unsubstituted or $C_1$-$C_{12}$alkyl-substituted phenyl, a

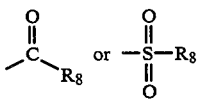

radical, where, in addition, the two $R_9$ radicals in —$N(R_9)_2$ are identical or different and, together with the nitrogen atom to which they are bonded, may form a 5- or 6-membered heterocyclic ring which, in addition to the nitrogen atom, may also contain further nitrogen, oxygen or sulfur atoms, or the two $R_9$ radicals, together with the nitrogen atom to which they are bonded, form a

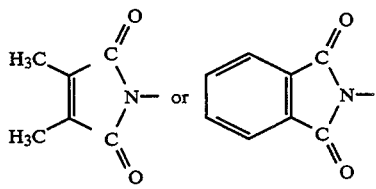

radical, $R_{10}$ is as defined for $R_9$ or additionally is naphthyl, biphenylyl, pyridyl or pyrimidinyl, these radicals being unsubstituted or substituted by Cl, Br, I, $NO_2$, $C_1$-$C_{12}$alkyl, $C_1$-$C_{10}$alkoxy, $C_1$-$C_8$alkylthio, phenylthio, morpholino or —$N(C_1$-$C_4$alkyl$)_2$, or $R_{10}$ is phenyl which is substituted by Cl, Br, I, $NO_2$, $C_1$-$C_{10}$alkoxy, $C_1$-$C_8$alkylthio, phenylthio, morpholino or —$N(C_1$-$C_4$alkyl$)_2$, X os —O—, —S—,

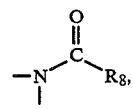

methylene or ethylene, and

A is $C_1$-$C_{12}$alkylene or —X—A—X— is a direct bond.

The $R_1$ groups are preferably identical radicals. Suitable substituents for $R_1$ are: linear or branched alkyl or alkoxy having 1 to 18, particularly 1 to 12 and in particular 1 to 6 carbon atoms, and alkenyl having 2 to 18, particularly 2 to 12, and in particular 2 to 6 carbon atoms, e.g. methyl, ethyl, propyl, isopropyl, n-butyl, t-butyl, pentyl, hexyl, octyl, decyl, dodecyl, tetradecyl, hexadecyl, octadecyl and corresponding alkenyl and alkoxy groups; cycloalkyl having 5 to 8 ring carbon atoms, e.g. cyclopentyl, cyclohexyl, cycloheptyl, methylcyclopentyl and methylcyclohexyl; phenyl and naphthyl, phenyl-substituted $C_1$-$C_{12}$alkyl, e.g. benzyl and phenylethyl; cyano and Cl, I and Br; —$Si(R_2)_3$ and —$Ge(R_2)_3$ in which $R_2$ is preferably $C_1$-$C_8$alkyl, cyclohexyl, phenyl or benzyl. Examples of alkyl $R_2$ are methyl, ethyl, n- and i-propyl, n-, i- and t-butyl, pentyl, hexyl, heptyl and octyl. The radicals $R_1$ may contain up to 5, but in particular up to 3 substituents. The two $R_1$ groups are preferably cyclopentadienyl$\ominus$ or methylcyclopentadienyl$\ominus$ radicals, in particular cyclopentadienyl$\ominus$ radicals.

Any $C_1$-$C_{12}$alkyl radicals are, for example, linear or branched $C_1$-$C_{12}$alkyl, preferably $C_1$-$C_8$alkyl, in particular $C_1$-$C_4$alkyl. Examples are methyl, ethyl and the isomers of propyl, butyl, pentyl, hexyl, heptyl, octyl, nonyl, decyl, undecyl and dodecyl. Tertiary $C_4$-$C_6$alkyl is, for example, t-butyl, 2-methylbut-2-yl, 2,3-dimethylbut-2-yl or 2-methylpent-2-yl.

$C_1$-$C_{12}$Alkylene A is methylene, ethylene, propylene, butylene, pentylene, hexylene, heptylene, octylene, nonylene, decylene, undecylene or dodecylene, preferably ethylene or methylene.

Examples of $C_1$-$C_4$alkoxy-substituted $C_1$-$C_{12}$alkyl radicals are methoxymethyl, ethoxymethyl, propoxymethyl, butoxymethyl, methoxyethyl, ethoxyethyl, butoxyethyl, propoxyethyl, methoxypropyl, ethoxypropyl, methoxybutyl, ethoxybutyl, methoxyhexyl, methoxyoctyl and methoxydodecyl.

Phenyl-substituted $C_1$-$C_{12}$alkyl is, for example, benzyl, 1,1-dimethylbenzyl, phenylethyl, phenylpropyl or phenylbutyl.

$C_1$-$C_4$Alkyl-$C_5$-$C_8$cycloalkyl is $C_5$-$C_8$cycloalkyl which is substituted by $C_1$-$C_4$alkyl, e.g. methylcyclopentyl or methylcyclohexyl.

$C_5$-$C_8$Cycloalkyl is, for example, cyclopentyl, cyclohexyl, cycloheptyl or cyclooctyl, preferably cyclopentyl or cyclohexyl.

Examples of $C_7$-$C_{12}$alkylphenyl-, $C_5$-$C_8$cycloalkyl- or $C_1$-$C_4$alkyl-$C_5$-$C_8$-cycloalkyl-substituted $C_1$-$C_8$alkyl are methylbenzyl, ethylbenzyl, butylbenzyl, 2,6-dimethylbenzyl, 2,4,6-trimethylbenzyl, 2,6-dimethylphenylethyl, -propyl or -butyl, 2,4,6-trimethylphenylethyl, -propyl or -butyl, 2,6-dimethylphenyl-α,α-dimethylethyl, 2,4,6-trimethylphenyl-α,α-dimethylethyl, cyclopentyl- or cyclohexylmethyl, cyclopentyl- or cyclohexylethyl, cyclopentyl- or cyclohexylpropyl, cyclopentyl- or cyclohexylbutyl, (methylcyclopentyl)methyl, (ethylcyclohexyl)methyl or -ethyl, (butylcyclopentyl)methyl, or (propylcyclohexyl)methyl or -ethyl.

α-Tertiary $C_4$–$C_6$alkyl is, for example, t-butyl, 1,1-dimethylprop-1-yl, 1,1,2-trimethylprop-1-yl or 1,1-dimethylbut-1-yl, preferably t-butyl.

Any $C_3$–$C_8$cycloalkyl substituents are, for example, cyclopropyl, cyclopentyl, cyclohexyl, cycloheptyl or cyclooctyl, in particular cyclopentyl or cyclohexyl, preferably cyclohexyl. $C_1$–$C_{12}$Alkyl-substituted $C_3$–$C_8$-cycloalkyl is, for example, methyl-, dimethyl-, ethyl-, n-propyl-, i-propyl-, n-butyl-, i-butyl-, t-butyl-, octyl- or dodecylcyclopentyl or -cyclohexyl.

$C_6$–$C_{20}$Cycloalkenylalkyl is, for example, cyclopentenyl-, cyclohexenyl- or cyclooctenylmethyl or -ethyl.

$C_1$–$C_{12}$Alkyl-, Cl-, Br-, I- or $C_1$–$C_4$alkoxy-substituted phenyl is monosubstituted or polysubstituted, particularly monosubstituted to trisubstituted, in particular monosubstituted or disubstituted, preferably monosubstituted phenyl. Examples of such radicals are tolyl, mesityl, xylyl, ethylphenyl, butylphenyl, dodecylphenyl, methoxyphenyl, dimethoxyphenyl, ethoxyphenyl, diethoxyphenyl, butoxyphenyl, chlorophenyl, dichlorophenyl and trichlorophenyl. Alkyl and alkoxy substituents on the phenyl substituent preferably have 1–4 carbon atoms.

$C_1$–$C_8$Alkylthio-, phenyl- or phenylthio-substituted phenyl $R_3$, $R_4$ or $R_5$ is monosubstituted or polysubstituted, particularly monosubstituted to trisubstituted, in particular monosubstituted or disubstituted, preferably monosubstituted phenyl. The substituents are in the 3-, 4-, 3,4- or 3,4,5-position, preferably in the 4-position, of the phenyl ring.

Any $C_2$–$C_{12}$alkenyl radicals are, for example, linear or branched $C_2$–$C_{12}$alkenyl, preferably $C_2$–$C_8$alkenyl, in particular $C_2$–$C_4$alkenyl. The alkenyl may be monounsaturated or polyunsaturated. Examples are allyl, methallyl, 1,1-dimethylallyl, butenyl, hexenyl, octenyl, 2,5,8-trimethylnona-2,7-dien-5-yl, undecenyl and dodecenyl, preferably allyl and methallyl. $C_2$–$C_{12}$Alkenyl $R_5$ is, in particular, 2,5,8-trimethylnona-2,7-dien-5-yl.

$C_1$–$C_{12}$Alkoxy is, for example, linear or branched. Preference is given to $C_1$–$C_8$alkoxy, in particular $C_1$–$C_6$alkoxy and particularly $C_1$–$C_4$alkoxy. Examples are methoxy, ethoxy and the isomers of propoxy, butoxy, pentoxy, hexyloxy, heptyloxy, octyloxy, nonyloxy, decyloxy, undecyloxy and dodecyloxy. $C_2$–$C_{12}$Alkoxy which is interrupted by one or more oxygen atoms is, for example, the —O—CH$_2$—OCH$_3$, —O—CH$_2$—OC$_2$H$_5$, —O—(CH$_2$—O)$_x$—CH$_3$, —O—(CH$_2$—O)$_x$—C$_2$H$_5$, —O—(CH$_2$CH$_2$—O)$_x$—CH$_3$ or —O—(CH$_2$CH$_2$—O)$_x$—C$_2$H$_5$ group, where x is a number from 1 to 20. $C_2$–$C_{12}$Alkoxy which is interrupted by oxygen atoms is in particular —O—CH$_2$—OCH$_3$.

$C_5$–$C_8$Cycloalkyl-substituted $C_1$–$C_{12}$alkoxy is, for example, cyclohexylmethoxy, cyclopentylmethoxy, cyclohexylethoxy or cyclopentylethoxy, preferably cyclohexylmethoxy. Phenoxy-substituted $C_1$–$C_{12}$alkoxy is, for example, phenoxymethoxy, phenoxyethoxy, phenoxybutoxy or phenoxyoctyloxy, preferably phenoxyethoxy.

$C_3$–$C_{12}$Cycloalkoxy is, for example, cyclopropoxy, cyclopentoxy, cyclohexyloxy, cycloheptyloxy, cyclooctyloxy or cyclododecyloxy, in particular cyclopentoxy or cyclohexyloxy, preferably cyclohexyloxy. If these radicals are substituted by $C_1$–$C_4$alkyl, they are monosubstituted to tetrasubstituted, in particular monosubstituted to trisubstituted, preferably monosubstituted. These radicals are, for example, methylcyclohexyloxy, methylcyclopentyloxy, dimethylcyclohexyloxy, ethylcyclohexyloxy, diethylcyclohexyloxy, propylcyclohexyloxy or butylcyclohexyloxy.

$C_1$–$C_4$Alkoxy-substituted phenoxy is monosubstituted to tetrasubstituted, in particular monosubstituted to trisubstituted, preferably monosubstituted or disubstituted. Examples of such radicals are 2,6-dimethoxyphenoxy, 2,4-dimethoxyphenoxy, 2,4,6-trimethoxyphenoxy, 4-methoxyphenoxy, 2-methoxyphenoxy, 6-methoxyphenoxy, 2,6-diethoxyphenoxy, 2,4-diethoxyphenoxy, 2-ethoxyphenoxy, 4-ethoxyphenoxy, 6-ethoxyphenoxy, propoxyphenoxy or butoxyphenoxy.

$C_1$–$C_4$Alkyl-substituted phenoxy is monosubstituted to tetrasubstituted, in particular monosubstituted to trisubstituted, preferably monosubstituted or disubstituted. Examples of such radicals are 2,6-dimethylphenoxy, 2,4-dimethylphenoxy, 2,4,6-trimethylphenoxy, 4-methylphenoxy, 2-methylphenoxy, 6-methylphenoxy, 2,6-diethylphenoxy, 2,4-diethylphenoxy, 2-ethylphenoxy, 4-ethylphenoxy, 6-ethylphenoxy, propylphenoxy or butylphenoxy.

$C_1$–$C_4$Alkyl-substituted benzyloxy is monosubstituted to tetrasubstituted, in particular monosubstituted to trisubstituted, preferably monosubstituted or disubstituted. The alkyl substituents may be positioned both on the methylene and on the aromatic ring of the benzyloxy radical. Examples of such radicals are 2-methylbenzyloxy, 4-methylbenzyloxy, 6-methylbenzyloxy, 2,4-dimethylbenzyloxy, 2,6-dimethylbenzyloxy, 2,6-diethylbenzyloxy, 2,4-diethylbenzyloxy, propylbenzyloxy, butylbenzyloxy, 1-methyl-1-phenylmethoxy, 1,1-dimethyl-1-phenylmethoxy or 1-methyl-1-(2,6-dimethylphenyl)-methoxy.

$C_2$–$C_6$Alkenyloxy contains, for example, linear or branched alkenyl radicals. Preference is given to $C_2$–$C_4$alkenyloxy- Examples are allyloxy, methallyloxy, 1,1-dimethylallyloxy, butenyloxy, hexenyloxy, octenyloxy, undecenyloxy and dodecenyloxy, preferably allyloxy and methallyloxy.

Any $C_1$–$C_8$alkylthio substituents are, for example, methylthio, ethylthio or isomers of propylthio, butylthio, pentylthio, hexylthio, heptylthio or octylthio. Preference is given to $C_1$–$C_6$alkylthio, in particular $C_1$–$C_4$alkylthio, for example i-butylthio. $C_3$–$C_8$Cycloalkylthio is $C_3$–$C_8$cycloalkyl-S-, where the cycloalkyl radicals are defined as described above apart from the corresponding number of carbon atoms. Substituted benzylthio and phenylthio may be, for example, monosubstituted to trisubstituted, for example monosubstituted or disubstituted, in particular monosubstituted, by $C_1$–$C_4$alkoxy and/or $C_1$–$C_4$alkyl. Examples are (4-methyl)-, (2,4-dimethyl)-, (2,4,6-trimethyl)-, (4-methoxy)-, (2,4-dimethoxy)-, (2,4,6-trimethoxy)-, (4-ethoxy)-, (2,4-diethoxy)-, (2,4,6-trimethoxy)-, (4-methoxy-2-methyl)-, (2,4-dimethoxy-6-methyl)-, (4-ethoxy-2-methyl)-, (2,4-diethoxy-6-methyl)benzylthio or -phenylthio.

Halogen is chlorine, bromine or iodine, in particular chlorine or bromine, preferably chlorine.

If the two $R_9$ radicals in $-N(R_9)_2$, together with the nitrogen atom to which they are bonded, form a 5- or 6-membered heterocyclic ring which, in addition to the nitrogen atom, may also contain further nitrogen, oxygen or sulfur atoms, these rings may be saturated or preferably unsaturated. They are, for example, pyrryl, dimethylpyrryl, piperidinyl, morpholinyl, piperazinyl, 4-methylpiperazinyl, diazolyl, thienyl, thiazolyl, imidazolyl or oxazolyl radicals.

$-N(C_1-C_4Alkyl)_2$ is, for example, dimethylamino, diethylamino, dipropylamino, dibutylamino or methylethylamino, in particularly dimethylamino.

$R_5$ is, for example, $C_1-C_{12}$alkyl, preferably $C_1-C_8$alkyl, for example $C_1-C_6$alkyl, in particular $C_1-C_4$alkyl, $C_3-C_8$cycloalkyl, in particular cyclohexyl or cyclopentyl, or adamantyl.

If $R_5$ is, for example, phenyl which is substituted by $-NR_8R_9$, $R_8$ and $R_9$ are preferably identical and are $C_1-C_4$alkyl, in particular methyl.

Substituted phenyl $R_{10}$ is phenyl which is monosubstituted or polysubstituted, particularly monosubstituted to trisubstituted, in particular monosubstituted or disubstituted, preferably monosubstituted phenyl. Examples of such radicals are tolyl, mesityl, xylyl, ethylphenyl, butylphenyl, dodecylphenyl, methoxyphenyl, dimethoxyphenyl, ethoxyphenyl, diethoxyphenyl, butoxyphenyl, chlorophenyl, dichlorophenyl, trichlorophenyl, morpholinophenyl and dimethylaminophenyl. Alkyl substituents on the phenyl substituent preferably have 1-4 carbon atoms.

The compounds of the formula I are generally prepared by reacting a titanocene dihalide with the radical Q in the presence of a strong base:

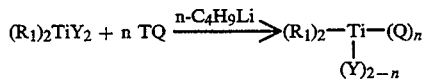

$R_1$, Q and n are as defined in claim 1. Y is chlorine, bromine or iodine, and T is hydrogen or bromine.

Titanocenes where $Y=CN$ or SCN are prepared by substitution reactions from the corresponding titanocene where $Y=Cl$.

Titanocenes where $Y=-O-CO-CH_3$, $-O-C-$phenyl or $-O-SO_2-CH_3$ are prepared analogously to the method described in U.S. Pat. No. 4,713,401 for fluorine-containing titanocenes.

The compounds of the formula I (3) in which Q is a pyrimidine radical are prepared, for example, by reacting a titanocene dihalide (1) with a substituted pyrimidine (2) in the presence of a strong base:

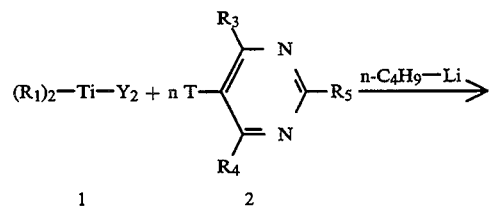

-continued

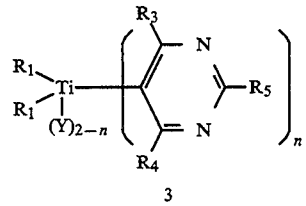

(n, $R_1$, $R_3$, $R_4$ and $R_5$ are as defined in the claims, T is hydrogen or Br, and Y is Cl, Br or I). Reactions of this type have been described, for example, by M. D. Mehta, D. Miller and M. F. Mooney in J. Chem. Soc. (1965), 6695. Further information on such reactions is given by D. J. Brown, The Pyrimidines, Suppl. 1, 159, or Suppl. 2, 219, Interscience publishers, John Wiley & Sons, New York/London, 1962.

In the reactions described above, the bases used can also be, for example, s-butyllithium, t-butyllithium or magnesium metal.

In the preparation of the titanocenes containing tris-ether pyrimidine radicals ($R_3$, $R_4$ and $R_5=-OR$), it should be noted that T in the compound (2) must be Br, since the corresponding unbrominated tris-ether pyrimidine is not directly deprotonated by butyllithium. The corresponding pyrimidine is thus brominated in the 5-position before the reaction with butyllithium and the $(R_1)_2-TiY_2$ (cf. J. Chem. Soc. 1965, 5467-73).

U.S. Pat. No. 5,075,467 describes a process for the preparation of fluorinated titanocenes in which a titanocene dihalide is reacted with a fluorinated and possibly additionally substituted phenyl in the presence of lithium amide at from $-30°$ to $+25°$ C. It is, for example, also possible to prepare the compounds according to the invention analogously to this process.

The pyrimidine compounds (2) can be obtained, for example, by chlorinating barbituric acid using $POCl_3$ and then reacting the chlorinated product with sodium alkoxides. Selection of the appropriate stoichiometry and reaction conditions allows the dichloromonoether, monochlorodiether or trisether compounds to be obtained (cf. J. Baddiley and A. Tapham, J. Chem. Soc. 1944, 679, and D. J. Brown, The Pyrimidines, Chapter IV, 202, Interscience publishers, John Wiley & Sons, New York/London 1962). Synthesis of 4,6-dichloro-2-arylpyrimidines is described, for example, by J. A. Hendry and R. F. Homer in J. Chem. Soc. (1952), 328-333.

The compounds (2) containing thioether radicals are prepared by reacting the corresponding chlorine-substituted pyrimidines with the corresponding mercaptans in the presence of a base, preferably sodium hydride. An example of the preparation of a compound of this type containing the thioether radical in the 2-position is:

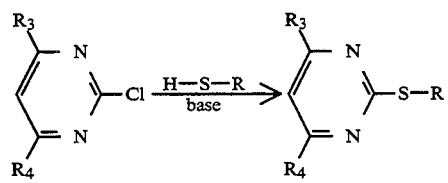

$R_3$ and $R_4$ are as defined above, and R is $C_1-C_8$alkyl, or unsubstituted or substituted benzyl or phenyl.

The corresponding compounds containing a sulfone radical are prepared, for example, from the above-described alkylthioether compounds by oxidation using m-chloroperbenzoic acid.

2-Alkylpyrimidines can be prepared, for example, from alkyl nitriles via alkylamidines by the method described by D. J. Brown in Australian J. Chem., (1977) 30, 1785-1791.

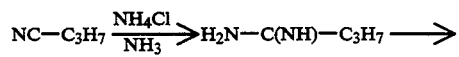

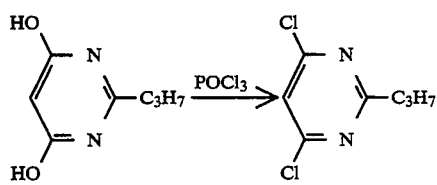

The pyrimidines containing

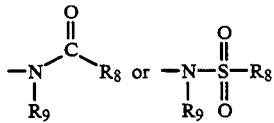

substituents are prepared, for example, by reacting a chlorinated pyrimidine with a secondary amine and then N-acylating the product.

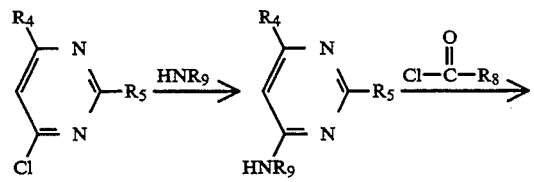

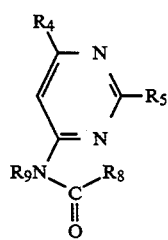

Another possibility is to start, for example, from an aminopyrimidine, which is first alkylated and then acylated.

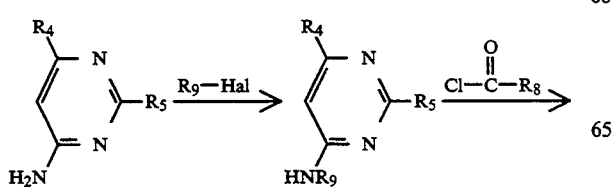

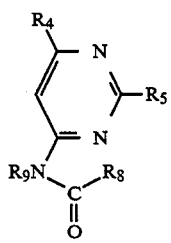

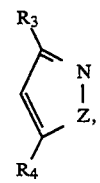

(Hal is halogen, and $R_4$, $R_5$, $R_8$ and $R_9$ are as defined above).

The preparation of chlorinated pyrimidines and aminopyrimidines is known in general terms.

The preparation of five-membered rings containing two hetero atoms

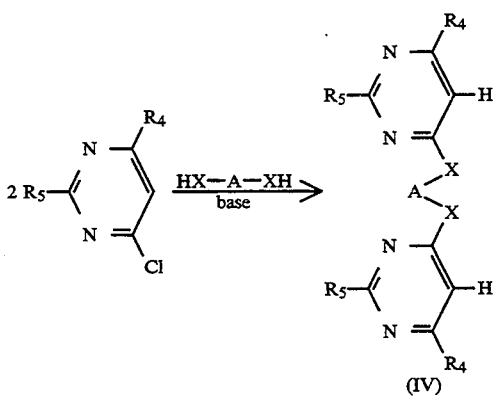

in which $R_3$, $R_4$ and Z are as defined above, is known in general terms to persons skilled in the art and is described in a number of publications, such as, for example, J. Chem. Soc. C (1968), 466; Synthetic Commun. 20 (1990), 3213-3218; Izv. Akad. Nauk, SSSR, Ser. Khim. (1990) 3, 640, 645; Bull. Chem. Soc. Jpn (1991) 2, 719-20; Synthetic Comm. 20 (1990), 3161-3166; Synthetic Comm. 20 (1990), 2799-2804; J. Chem. Soc., Chem. Comm. (1991), 17-18; Can. J. Chem. 69 (1991), 625-631; Advances in Heterocyclic Chemistry (1979) 25, 154, 159, 171; J. Chem. Soc. C (1968), 172; Chem. Pharm. Bulletin 16 (1968), 148 or the reviews by A. N. Kost and I. J. Grandberg in Advances in Heterocyclic Chemistry (1966) 6, 370ff; B. J. Wakefield und D. J. Wright in Advances in Heterocyclic Chemistry (1979) 25, 148ff or K. R. H. Wooldridge Advances in Heterocyclic Chemistry (1972) 14, 12, 20, 29.

The starting materials (IV) for the preparation of compounds of the formula II in which X is —O— or —S— can be prepared, for example, by reacting 2 equivalents of a substituted pyrimidine with one equivalent of an alkylenediol or alkylenethiol in the presence of 2 equivalents of a base:

The starting materials (V) for the preparation of compounds of the formula II in which X is

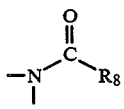

can be obtained, for example, by reacting 2 equivalents of a substituted pyrimidine with one equivalent of the corresponding bisaminoalkylene in the presence of 2 equivalents of a base and subsequently acylating the product:

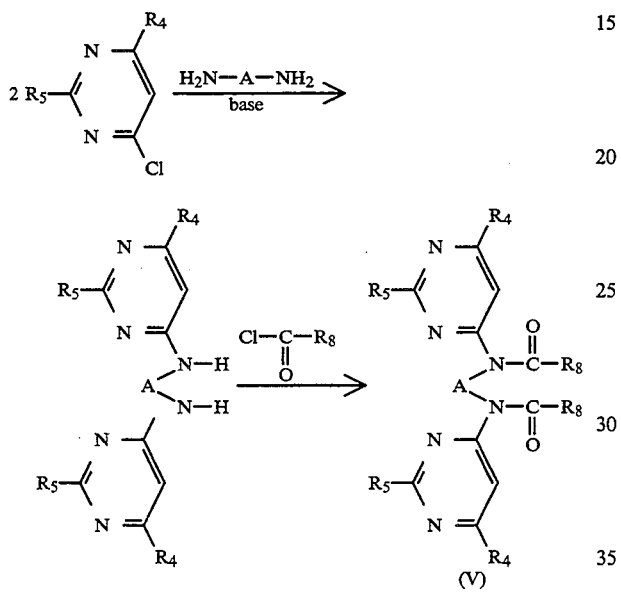

The starting materials (VI) for the preparation of compounds of the formula II in which X is methylene, ethylene or a direct bond is carried out, for example, by reacting one equivalent of the corresponding tetraketone with two equivalents of an amidine:

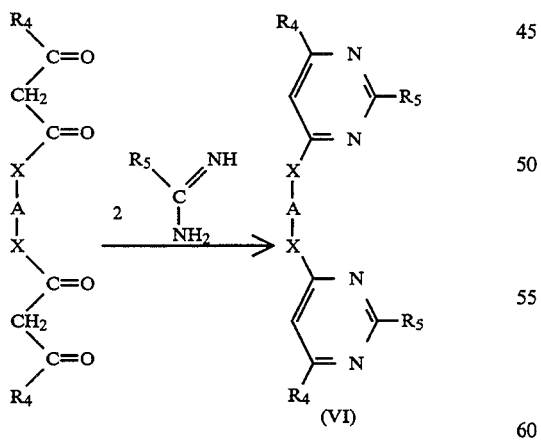

The compounds of the formula II are then prepared analogously to the compounds of the formula I by reaction with $(R_1)_2TiY_2$ by replacing the pyrimidine used with the corresponding compound of the formula IV, V or VI. The reactants are expediently employed here in a ratio of 1:1.

Also interesting are compounds of the formula

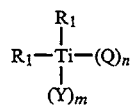

(I) in which both $R_1$ radicals are, independently of one another, cyclopentadienyl⊖, indenyl⊖ or 4,5,6,7-tetrahydroindenyl⊖, these radicals being unsubstituted or substituted by $C_1$–$C_{18}$alkyl, $C_1$–$C_{18}$alkoxy, $C_2$–$C_{18}$alkenyl, $C_5$–$C_8$cycloalkyl, $C_1$–$C_4$alkyl-$C_5$–$C_8$cycloalkyl, phenyl, naphthyl, phenyl-substituted $C_1$–$C_{12}$alkyl, —Si($R_2$)$_3$, —Ge($R_2$)$_3$, cyano, Cl, Br or I, and the two $R_2$ radicals, independently of one another, are $C_1$–$C_{12}$alkyl, $C_5$–$C_8$cycloalkyl, or unsubstituted or $C_1$–$C_6$alkyl-substituted phenyl or benzyl,

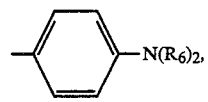

radical,
Z is —$NR_{10}$—, —O— or —S—,
Y is Cl, Br, I, CN, SCN or —O—$SO_2$—$CH_3$,
n is 1 or 2,
m is 0 or 1, where the sum of n and m must be 2,
$R_3$, $R_4$ and $R_5$, independently of one another, are hydrogen, Cl, Br, I, unsubstituted or $C_1$–$C_4$alkoxy- or phenyl-substituted $C_1$–$C_{12}$alkyl, unsubstituted or $C_1$–$C_4$alkyl-substituted $C_3$–$C_8$cycloalkyl, unsubstituted or $C_1$–$C_{12}$alkyl-, Cl-, Br-, I-, $C_1$–$C_8$alkylthio-, —$NR_8R_9$— or $C_1$–$C_{10}$alkoxy-substituted phenyl, pyrryl, furyl, thienyl, imidazolyl or pyridyl, or $R_3$, $R_4$ and $R_5$ are unsubstituted $C_2$–$C_{12}$alkenyl or $C_2$–$C_{12}$alkenyl which is substituted by unsubstituted or $C_1$–$C_4$alkyl-, $C_1$–$C_4$alkoxy-, $C_1$–$C_4$alkylthio-, Cl-, Br- or I-substituted phenyl or —⟨phenyl⟩—$N(R_6)_2$, or $R_3$, $R_4$ and $R_5$ are unsubstituted or $C_5$–$C_8$cycloalkyl-substituted $C_1$–$C_{12}$alkoxy, $C_2$–$C_{12}$alkoxy which is interrupted by one or more oxygen atoms, unsubstituted or $C_1$–$C_4$alkyl-substituted $C_3$–$C_{12}$cycloalkoxy, unsubstituted or $C_1$–$C_4$alkoxy- or $C_1$–$C_4$alkyl-substituted phenoxy, unsubstituted or $C_1$–$C_4$alkyl-substituted benzyloxy, tetrahydrofurfuryloxy, $C_2$–$C_6$alkenyloxy, —O—Si—($R_7$)$_3$, $C_1$–$C_8$alkylthio, $C_3$–$C_8$cycloalkylthio, unsubstituted or $C_1$–$C_4$alkyl- and/or $C_1$–$C_4$alkoxy-substituted benzylthio, unsubstituted or $C_1$–$C_4$alkyl- and/or $C_1$–$C_4$alkoxy-substituted thiophenyl, —S(O)$R_8$, —$SO_2R_8$, —N($R_9$)$_2$,

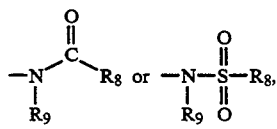

where $R_3$ and $R_4$ are not simultaneously hydrogen, and at least one radical $R_3$ or $R_4$ in the

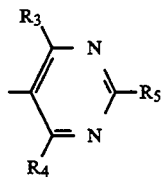

radical is unsubstituted or $C_5$–$C_8$cycloalkyl-substituted $C_1$–$C_{12}$alkoxy, $C_2$–$C_{12}$alkoxy which is interrupted by one or more oxygen atoms, unsubstituted or $C_1$–$C_4$alkyl-substituted $C_3$–$C_{12}$cycloalkoxy, unsubstituted or $C_1$–$C_4$alkoxy- or $C_1$–$C_4$alkyl-substituted phenoxy, unsubstituted or $C_1$–$C_4$alkyl-substituted benzyloxy, tetrahydrofurfuryloxy or $C_2$–$C_6$alkenyloxy, and in the case where Z is —$NR_{10}$—, $R_3$ and $R_4$ are Cl, Br or I, the two $R_6$ radicals, independently of one another, are $C_1$–$C_4$alkyl or $C_2$–$C_{10}$alkenyl, or the two $R_6$ radicals, together with the nitrogen atom to which they are bonded, form a morpholino radical, $R_7$ is $C_1$–$C_{12}$alkyl, $C_5$–$C_8$cycloalkyl or unsubstituted or $C_1$–$C_6$alkyl-substituted phenyl, $R_8$ is unsubstituted or $C_1$–$C_4$alkyl-substituted phenyl or α-tertiary $C_4$–$C_6$alkyl, $R_9$ is unsubstituted or phenyl-, $C_7$–$C_{12}$alkylphenyl-, $C_5$–$C_8$cycloalkyl- or $C_1$–$C_4$alkyl-$C_5$–$C_8$cycloalkyl-substituted $C_1$–$C_8$alkyl, $C_2$–$C_8$alkenyl, unsubstituted or $C_1$–$C_4$alkyl-substituted $C_5$–$C_8$cycloalkyl, $C_6$–$C_{20}$cycloalkenylalkyl, unsubstituted or $C_1$–$C_{12}$alkyl-substituted phenyl, a

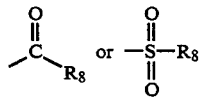

radical, where, in addition, the two $R_9$ radicals in —$N(R_9)_2$ are identical or different and, together with the nitrogen atom to which they are bonded, may form a 5- or 6-membered heterocyclic ring which, in addition to the nitrogen atom, may also contain further nitrogen, oxygen or sulfur atoms, or, if the two $R_9$ radicals are a

group, the two $R_9$ radicals, together with the nitrogen atom to which they are bonded, form a

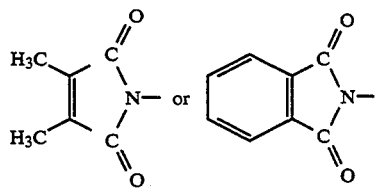

radical, $R_{10}$ is as defined for $R_9$, and if n=2, the formula I also includes compounds of the formula II

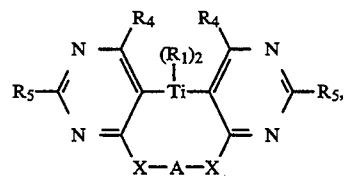

in which X is —O—, —S—,

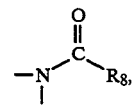

methylene or ethylene, and A is $C_1$–$C_{12}$alkylene or —X—A—X— is a direct bond.

Preference is given to compounds of the formulae I and II in which both $R_1$ radicals, independently of one another, are cyclopentadienyl⊖ which is unsubstituted or substituted by $C_1$–$C_{18}$alkyl, $C_1$–$C_{18}$alkoxy, $C_2$–$C_{18}$alkenyl, —Si($R_2$)$_3$ or Cl, Br, I, in particular $C_1$–$C_4$alkyl.

Further interesting compounds of the formulae I and II are those in which $R_3$ and $R_5$ are unsubstituted or $C_5$–$C_8$cycloalkyl- or phenoxy-substituted $C_1$–$C_{12}$alkoxy, $C_2$–$C_{12}$alkoxy which is interrupted by one or more oxygen atoms, unsubstituted or $C_1$–$C_4$alkyl-substituted $C_3$–$C_{12}$cycloalkoxy, unsubstituted or $C_1$–$C_4$alkoxy- and/or $C_1$–$C_4$alkyl-substituted phenoxy, unsubstituted or $C_1$–$C_4$alkyl-substituted benzyloxy, tetrahydrofurfuryloxy or $C_2$–$C_6$alkenyloxy.

Particular preference is given to compounds in which $R_3$ and $R_5$ are unsubstituted or cyclohexyl- or phenoxy-substituted $C_1$–$C_{12}$alkoxy, $C_2$–$C_{12}$alkoxy which is interrupted by one or more oxygen atoms, unsubstituted or $C_1$–$C_4$alkyl-substituted $C_5$–$C_8$cycloalkoxy, unsubstituted or $C_1$–$C_4$alkoxy-substituted phenoxy, unsubstituted or $C_1$–$C_4$alkyl-substituted benzyloxy, tetrahydrofurfuryl or $C_2$–$C_6$alkenyloxy.

Also interesting are compounds of the formulae I and II in which $R_5$ is $C_1$–$C_8$alkylthio, $C_3$–$C_8$cycloalkylthio, unsubstituted or $C_1$–$C_4$alkyl- and/or $C_1$–$C_4$alkoxy-substituted benzylthio, unsubstituted or $C_1$–$C_4$alkyl- and/or $C_1$–$C_4$alkoxy-substituted phenylthio, —S(O)$R_8$ or —SO$_2R_8$, in particular $C_1$–$C_8$akylthio.

Particularly interesting compounds are those in which Q is a

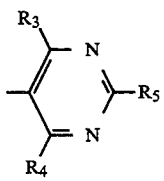

radical.

Preference is also given to compounds in which $R_4$ is Cl, Br or I, in particular Cl.

Further preferred compounds of the formula I are those in which n=2 and m=0.

Also interesting are compounds of the formula I in which n and m are 1.

Preference is also given to compounds of the formula I in which Y is Cl, Br or I, in particular Cl.

Other preferred compounds are those in which $R_3$, $R_4$ and $R_5$, independently of one another, are unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy.

In further interesting compounds of the formulae I and II, $R_5$ is phenyl, pyrryl, furyl, thienyl, imidazolyl, pyridyl, naphthyl, anthryl, phenanthryl or biphenylyl, where the radicals phenyl, pyrryl, furyl, thienyl, imidazolyl, pyridyl, naphthyl, anthryl, phenanthryl and biphenylyl are unsubstituted or substituted by $C_1$-$C_{12}$alkyl, cyclopentyl, cyclohexyl, Cl, Br, I, $C_1$-$C_8$alkylthio, —$NR_8R_9$, phenyl, phenylthio or $C_1$-$C_{10}$alkoxy.

Other important compounds are those in which $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy, $R_4$ is Cl, and $R_5$ is phenyl which is unsubstituted or substituted by $C_1$-$C_{12}$alkyl, Cl, Br, $C_1$-$C_8$alkylthio, —$NR_8R_9$, phenyl, phenylthio or $C_1$-$C_{10}$alkoxy.

Likewise interesting are the compounds in which $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy, $R_4$ is Cl, and $R_5$ is $C_1$-$C_{12}$alkyl, $C_3$-$C_8$cycloalkyl or adamantyl.

Particular mention should be made of compounds of the formula I in which

Y is Cl, —O—CO—$CH_3$ or —O—CO—phenyl, $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, $C_5$-$C_8$cycloalkoxy, benzyloxy, tetrahydrofurfuryloxy or Cl, $R_4$ is as defined for $R_3$ or additionally hydrogen, and $R_5$ is as defined for $R_3$ or additionally hydrogen, $C_1$-$C_{12}$alkyl, $C_1$-$C_8$alkylthio, pyrryl, or phenyl which is unsubstituted or substituted by Cl, $C_1$-$C_1$-oalkoxy, phenyl, $C_1$-$C_8$alkylthio, phenylthio or —$NR_8R_9$, and $R_{10}$ is phenyl.

Preference is given to compounds of the formula I.

Particular mention should also be made of compounds of the formula I in which Q is

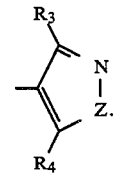

Preferred compounds of the formula I in which Q is

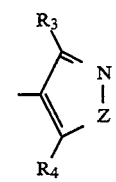

are those in which $R_3$ and $R_4$ are Cl,

Z is —$NR_{10}$—, and $R_{10}$ is phenyl which is unsubstituted or substituted by Cl, Br, I, $NO_2$, $C_1$-$C_{12}$alkyl, $C_1$-$C_{10}$alkoxy, $C_1$-$C_8$alkylthio, phenylthio, morpholino or —$N(C_1$-$C_4$alkyl$)_2$.

The compounds of the formulae I and II according to the invention may, due to certain substituents, be in the form of a number of different conformational isomers. The invention covers all conformational is, omen formed.

The compounds of the formulae I and II can be used according to the invention as photoinitiators for the photopolymerisation of ethylenically unsaturated compounds or mixtures which contain such compounds.

This use may also take place in combination with another photoinitiator and/or other additives.

The invention therefore also relates to photopolymerisable compositions comprising (a) at least one ethylenically unsaturated photopolymerisable compound and (b), as photoinitiator, at least one compound of the formula I or II, it also being possible for the composition to contain another photoinitiator (c) and/or other additives.

Examples of suitable photoinitiators (c) are those of the titanocene type which do not conform to the formula I or II, benzoin alkyl ethers, benzophenones, benzil ketals, 4-aroyl- 1,3-dioxolanes, dialkoxyacetophenones, α-hydroxy- or α-aminoacetophenones, α-hydroxycycloalkyl phenyl ketones, mono- or bisacylphosphine oxides, or mixtures thereof.

Mixtures of these photoinitiators (c) with titanocenes are described, for example, in EP-A-242 330 and U.S. Pat. No. 4,960,746. The novel titanocenes of the formulae I and II according to the invention may likewise be used as the titanocene component in the mixtures described therein.

If, in addition to the photoinitiator (b), the compositions according to the invention also contain one or more further photoinitiators (c), the weight ratio between the two components (c) and (b) can be, for example, from 1:1 to 30:1, preferably from 5:1 to 15:1.

The unsaturated compounds can contain one or more olefinic double bonds. They can be of low molecular weight (monomeric) or relatively high molecular weight (oligomeric). Examples of monomers containing one double bond are alkyl or hydroxyalkyl acrylates or methacrylates, e.g. methyl, ethyl, butyl, 2-ethylhexyl and 2-hydroxyethyl acrylate, isobornyl acrylate and methyl and ethyl methacrylate. Also interesting are silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halostyrenes, N-vinylpyrrolidone, vinyl chloride and vinylidene chloride.

Examples of monomers containing more than one double bond are ethylene glycol diacrylate, propylene glycol diacrylate, neopentyl glycol diacrylate, hexamethylene glycol diacrylate, bisphenol A diacrylate, 4,4'-bis(2-acryloyloxymethoxy)diphenylpropane, trimethylolpropane triacrylate, pentaerythritol triacrylate and tetraacrylate, vinyl acrylate, divinylbenzene, divinyl succinate, diallyl phthalate, triallyl phosphate, triallyl isocyanurate and tris(2-acryloylethyl)isocyanurate.

Examples of relatively high-molecular-weight (oligomeric), polyunsaturated compounds are acrylated epoxy resins, acrylated or vinyl ether- or epoxy-groups containing polyesters, polyurethanes and polyethers. Further examples of unsaturated oligomers are unsaturated polyester resins, which are usually prepared from maleic acid, phthalic acid and one or more diols and have molecular weights of from about 500 to 3000. In addition vinylether-monomers and -oligomers, as well as maleat-terminated oligomers with polyester-, polyurethane-, polyether-, polyvinyl ether- and epoxy-main chains can be used. Especially combinations of oligomers containing vinylether groups and polymers, as are described in WO 90/01512, are suitable. Copolymers of monomers functionalized with vinylether or maleic acid are suitable, too. Unsaturated oligomers of this type can also be termed prepolymers.

Particularly suitable compounds are, for example, esters of ethylenically unsaturated carboxylic acids and polyols or polyepoxides, and polymers containing ethylenically unsaturated groups in the chain or in side groups, e.g. unsaturated polyesters, polyamides and polyurethanes, and copolymers thereof, polybutadiene and butadiene copolymers, polyisoprene and isoprene copolymers, polymers and copolymers containing (meth)acrylic groups in side chains, and mixtures of one or more of such polymers.

Examples of unsaturated carboxylic acids are acrylic acid, methacrylic acid, crotonic acid, itaconic acid, cinnamic acid, unsaturated fatty acids, such as linolenic acid or oleic acid. Preference is given to acrylic and methacrylic acids.

Suitable polyols are aromatic and in particular aliphatic and cycloaliphatic polyols. Examples of aromatic polyols are hydroquinone, 4,4'-dihydroxybiphenyl, 2,2-di(4-hydroxyphenyl)propane, and novolaks and resols. Examples of polyepoxides are those based on said polyols, in particular the aromatic polyols, and epichlorohydrin. Other suitable polyols are polymers and copolymers containing hydroxyl groups in the polymer chain or in side groups, e.g. polyvinyl alcohol and copolymers thereof, or hydroxyalkyl polymethacrylates or copolymers thereof. Other suitable polyols are oligoesters containing hydroxyl terminal groups.

Examples of aliphatic and cycloaliphatic polyols are alkylenediols, preferably having 2 to 12 carbon atoms, such as ethylene glycol, 1,2- and 1,3-propanediol, 1,2-, 1,3- and 1,4-butanediol, pentanediol, hexanediol, octanediol, dodecanediol, diethylene glycol, triethylene glycol, polyethylene glycols having molecular weights of, preferably, 200 to 1500, 1,3-cyclopentanediol, 1,2-, 1,3-and 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be partially or fully esterified with one or more than one unsaturated carboxylic acid, where the free hydroxyl groups in partial esters may, for example, be etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, modified pentaerythritol triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, and bisacrylates and bismethacrylates of polyethylene glycol having molecular weights of from 200 to 1500, or mixtures thereof.

Suitable compounds as component (a) are also the amides of identical or different unsaturated carboxylic acids of aromatic, cycloaliphatic and aliphatic polyamines, preferably having 2 to 6, in particular 2 to 4, amino groups. Examples of such polyamines are ethylenediamine, 1,2- and 1,3-propylenediamine, 1,2-, 1,3- and 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-($\beta$-aminoethyl ether, diethylenetriamine, triethylenetetramine, di($\beta$-aminoethoxy)- and di($\beta$-aminopropoxy)ethane. Other suitable polyamines are polymers and copolymers, if desired with additional amino groups in the side chain and oligoamides containing amino terminal groups. Examples of unsaturated amides of this type are: methylenebisacrylamide, 1,6-hexamethylenebisacrylamide, diethylenetriaminetrismethacrylamide, bis(methacrylamidopropoxy)ethane, $\beta$-methacrylamidoethyl methacrylate, N[($\beta$-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, e.g.

styrene. The polyesters and polyamides may also be derived from dicarboxylic acids and ethylenically unsaturated diols or diamines, in particular relatively long-chain diols or diamines having, for example, 6 to 20 carbon atoms. Examples of polyurethanes are those built up from saturated or unsaturated diisocyanates and unsaturated or saturatediols.

Polybutadiene and polyisoprene and copolymers thereof are known. Examples of suitable comonomers are olefins, such as ethylene, propene, butene, hexene, (meth)acrylates, acrylonitrile, styrene and vinyl chloride. Polymers containing (meth)acrylate groups in the side chain are likewise known. These may be, for example, products of the reaction of novolak-based epoxy resins with (meth)acrylic acid, homopolymers or copolymers of vinyl alcohol or hydroxyalkyl derivatives thereof which have been esterified by means of (meth)acrylic acid, or homopolymers and copolymers of (meth)acrylates which have been esterified by means of hydroxyalkyl (meth)acrylates.

The photopolymerisable compounds can be employed alone or in any desired mixtures. Preference is given to mixtures of polyol (meth)acrylates.

It is also possible to add binders to the compositions according to the invention, which is particularly expedient if the photopolymerisable compounds are liquid or viscous substances. The amount of binder can be, for example, 5–95% by weight, preferably 10–90% by weight, in particular 40–90% by weight, based on the total solids content. The choice of binder depends on the area of application and the properties required therefor, such as developability in aqueous or organic solvent systems, adhesion to substrates and oxygen sensitivity.

Examples of suitable binders are polymers having a molecular weight of about 5000–2,000,000, preferably 10,000–1,000,000. Examples are: homopolymers and copolymers of acrylates and methacrylates, e.g. copolymers of methyl methacrylate-ethyl acrylate-methacrylic acid, poly(alkyl methacrylates), poly (alkyl acrylates); cellulose esters and ethers, such as cellulose acetate, cellulose acetate butyrate, methylcellulose and ethylcellulose; polyvinyl butyral, polyvinylformal, cyclised rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride-vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide) and polyesters, such as poly(ethylene glycol terephthalate) and poly(hexamethylene glycol succinate).

The unsaturated compounds can also be used as a mixture with non-photopolymerisable, film-forming components. These may be, for example, physically drying polymers or solutions thereof in organic solvents, e.g. nitrocellulose or cellulose acetobutyrate. However, they may also be chemically or thermally curable resins, e.g. polyisocyanates, polyepoxides or melamine resins. The additional use of thermally curable resins is important for use in so-called hybrid systems, which are photopolymerised in a first step and crosslinked by thermal aftertreatment in a second step.

In addition to the photoinitiator, the photopolymerisable mixtures may also contain various additives. Examples are thermal inhibitors, which are intended to prevent premature polymerisation, e.g. hydroquinone, hydroquinone derivatives, p-methoxyphenol, β-naphthol or sterically hindered phenols, e.g. 2,6-di(tert-butyl)-p-cresol. The shelf life in the dark can be increased by using, for example, copper compounds, such as copper naphthenate, stearate or octanoate, phosphorus compounds, e.g. triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. Atmospheric oxygen can be excluded during the polymerisation by adding paraffin or similar wax-like substances, which, on commencement of the polymerisation, migrate to the surface due to low solubility in the polymer and form a transparent surface layer which prevents contact with air. As light stabilisers, UV absorbers, e.g. those of the benzotriazole, benzophenone, oxanilide or hydroxyphenyl-s-triazine type, can be added in small amounts. Still better is the addition of light stabilisers which do not absorb UV light, e.g. sterically hindered amines (HALS).

The photopolymerisation can be accelerated by adding amines, e.g. triethanolamine, N-methyldiethanolamine, ethyl p-dimethylaminobenzoate or Michler's ketone. The effect of the amines can be increased by adding aromatic ketones of the benzophenone type. Amines which can be used as oxygen scavengers are, for example, substituted N,N-dialkylanilines, as described in EP-A-339 841. The photopolymerisation can also be accelerated by adding photosensitisers, which shift or broaden the spectral sensitivity. These are, in particular, aromatic carbonyl compounds, e.g. derivatives of benzophenone, thioxanthone, anthraquinone or 3-acylcoumarine, and 3-(aroylmethylene)thiazolines, but also eosin, rhodanine and erythrosine dyes.

The compositions according to the invention can also contain a photoreducible dye, e.g. xanthene, benzoxanthene, benzothioxanthene, thiazine, pyronine, porphyrin or acridine dyes, and/or a trihalomethyl compound which can be cleaved by radiation. Similar compositions are described, for example, in EP-A-445 624.

Further conventional additives are, depending on the application, optical brighteners, fillers, pigments, dyes, wetting agents and flow assistants. Thick and pigmented coatings can be cured by adding glass microbeads or powdered glass fibres, as described, for example, in U.S. Pat. No. 5,013,768.

The invention also relates to compositions in which component (a) is at least one ethylenically unsaturated, photopolymerisable compound dissolved or emulsified in water.

Aqueous radiation-curable prepolymer dispersions of this type are commercially available in many variants. This is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in a concentration of from 95 to 20% by weight, in particular from 70 to 40% by weight. The total of the percentages given for water and prepolymer in these compositions is in each case 100, and the assistants and additives are additional, in various amounts depending on the application.

The radiation-curable water-dispersed, frequently also dissolved, film-forming prepolymers are monofunctional or polyfunctional ethylenically unsaturated prepolymers which are known per se for aqueous prepolymer dispersions, can be initiated by free radicals and have, for example, a content of from 0.01 to 1.0 tool of polymerisable double bonds per 100 g of prepolymer, and a mean molecular weight of, for example, at least 400, in particular from 500 to 10,000. Depending on the application, however, prepolymers having higher molecular weights are also suitable. For example, polyesters containing polymerisable C—C double bonds and having an acid number of at most 10, polyethers containing polymerisable C—C double bonds, hydroxyl-containing products of the reaction of a polyepoxide containing at least two epoxide groups per molecule with at least one $\alpha,\beta$-ethylenically unsaturated carboxylic acid, polyurethane (meth)acrylates and acrylic copolymers containing $\alpha,\beta$-ethylenically unsaturated acrylic radicals, as described in EP-A-12 339, are used. It is also possible to use mixtures of these prepolymers. Also suitable are the polymerisable prepolymers described in EP-A-33 896, which are thioether adducts of polymerisable prepolymers having a mean molecular weight of at least 600, a carboxyl group content of from 0.2 to 15% and a content of from 0.01 to 0.8 mol of polymerisable C—C double bonds per 100 g of prepolymer. Other suitable aqueous dispersions based on specific alkyl (meth)acrylate polymers are described in EP-A-41 125, and suitable water-dispersible, radiation-curable prepolymers made from urethane acrylates are disclosed in DE-A-2 936 039.

Further additives which may be present in these aqueous radiation-curable prepolymer dispersions are dispersion aids, emulsifiers, antioxidants, light stabilisers, dyes, pigments, fillers, e.g. talc, gypsum, silica, ruffle, carbon black, zinc oxide, iron oxides, reaction accelerators, flow-control agents, lubricants, wetting agents, thickeners, matting agents, defoamers and other assistants which are customary in paint technology. Suitable dispersion aids are water-soluble, high-molecular-weight organic compounds containing polar groups, e.g. polyvinyl alcohols, polyvinylpyrrolidone and cellulose ethers. Emulsifiers which can be used are nonionic or possibly ionic emulsifiers.

The photopolymerisable compositions expediently contain the photoinitiator (b) in an amount of from 0.05 to 15% by weight, preferably from 0.2 to 5% by weight, based on the composition.

In certain cases, it may be advantageous to use mixtures of two or more of the photoinitiators according to the invention. It is of course also possible to use mixtures with known photoinitiators, e.g. mixtures with benzophenone, acetophenone derivatives, for example $\alpha$-hydroxycycloalkyl phenyl ketones, dialkoxyacetophenones, $\alpha$-hydroxy- or $\alpha$-aminoacetophenones, 4-aroyl-1,3-dioxolanes, benzoin alkyl ethers and benzil ketals, monoacylphosphine oxides, bisacylphosphine oxides and further titanocenes. If the photoinitiators according to the invention are used in hybrid systems, cationic photoinitiators, e.g. aromatic sulfonium or iodonium salts or cyclopentadienylarene iron(II) complex salts, are used in addition to the free-radical curing agents according to the invention.

The photopolymerisable compositions can be used for various purposes, for example as printing inks, varnishes, white paints, e.g. for wood or metal, coating materials, including for paper, wood, metal or plastic, daylight-curable coating material for building and road marking, for photographic reproduction processes, for holographic recording materials, for image-recording processes or for the production of printing plates which can be developed with organic solvents or in aqueous-alkaline media, for the production of masks for screen printing, as dental filling compositions, adhesives, pressure-sensitive adhesives, laminated resins, etch or permanent resists and solder resist masks for electronic circuits, for the production of three-dimensional articles by mass curing (UV curing in transparent moulds) or by the stereolithography process, as described, for example, in U.S. Pat. No. 4,575,330, for the production of composite materials (e.g. styrenic polyesters, which may also contain glass fibres and other assistants) and other thick-layer compositions, for coating or sealing electronic components, and as coatings for optical fibres. The compounds according to the invention may furthermore be used as initiators for emulsion polymerisation reactions, as initiators of polymerisation for the fixing of ordered states of liquid-crystalline monomers and oligomers, and for curing powder coatings.

In paints, mixtures of a prepolymer with polyunsaturated monomers and also a monounsaturated monomer are frequently used. The prepolymer here is primarily responsible for the properties of the paint film; by varying it, the person skilled in the art can modify the properties of the cured film. The polyunsaturated monomer functions as crosslinking agent, which makes the paint film insoluble. The monounsaturated monomer functions as reactive thinner, by means of which the viscosity is reduced without the need to use a solvent.

Unsaturated polyester resins are usually used in two-component systems together with a monounsaturated monomer, preferably styrene. In photoresists, specific one-component systems, e.g. polymaleimides, polychalcones or polyimides, as described in DE-A 2 308 830, are frequently used.

The photocurable compositions according to the invention are suitable, for example, as coating compositions for substrates of all types, e.g. wood, textiles, paper, ceramic, glass, plastics, such as polyesters, polyethylene terephthalates, polyolefins or cellulose acetate, in particular in the form of films, and metals, such as Al, Cu, Ni, Fe, Zn, Mg or Co and GaAs, Si or $SiO_2$, onto which a protective coating or, by imagewise exposure, an image is to be applied.

The substrates can be coated by applying a liquid composition, a solution or suspension to the substrate. The choice of solvent and concentration depend primarily on the nature of the composition and on the coating method. The solvent should be inert, i.e. it should not undergo any chemical reaction with the components and it should be removable again on drying after coating. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by known coating methods, e.g. by spin coating, dip coating, knife coating, curtain coating, brushing, spraying, in particular by electrostatic spraying, and reverse-roll coating. It is also possible to apply the photosensitive layer to a temporary, flexible carrier and then to coat the final substrate, e.g. a copper-laminated circuit board, by transferring the layer by lamination. The application rate (layer thickness) and the type of substrate (layer carrier) depend on the desired area of application. The layer thickness range is generally from about 0.1 μm to more than 10 μm.

The radiation-sensitive compositions according to the invention are used as negative resists which have very high photosensitivity and can be developed in aqueous alkaline media without swelling. They are suitable as photoresists for electronics (galvanoresists, etch resists and solder resists), for the production of printing plates, such as offset printing plates or screen printing plates, for chemical milling or as microresists in the production of integrated circuits. The possible layer carriers and the process conditions of the coated substrates vary correspondingly.

Films made from polyester, cellulose acetate or resin-coated papers, for example, are used for photographic image recording; specially treated aluminium is used for offset printing plates, copper laminates are used for the production of printed circuits, and silicone wafers are used for the production of integrated circuits. Layer thicknesses are generally from about 0.5 to 10 μm for photographic materials and offset printing plates and from 0.4 to about 2 μm for printed circuits.

After the substrates have been coated, the solvent is generally removed by drying, giving a photoresist layer on the carrier.

The term "imagewise" exposure includes both exposure through a photomask containing a predetermined pattern, for example a slide, exposure by a laser beam which is moved, for example, under computer control over the surface of the coated substrate, generating an image, and exposure to computer-controlled electron beams.

After the imagewise exposure of the material and before the development, it may be advantageous to carry out a brief thermal treatment. Only the exposed parts are thermocured. Temperatures used are generally 50°–150° C., preferably 80°–130° C.; the thermal treatment time is generally between 0.25 and 10 minutes.

The photocurable composition may furthermore be used in a process for the production of printing plates or photoresists, as described, for example, in DE-A-4 013 358. In this process, the composition is exposed briefly to visible light having a wavelength of at least 400 nm without a mask before, during or after the imagewise irradiation.

After the exposure and any thermal treatment, the unexposed areas of the photoresist are removed in a manner known per se using a developer.

The compositions according to the invention, as mentioned above, can be developed in aqueous-alkaline media. Suitable aqueous-alkaline developer solutions are, in particular, aqueous solutions of tetraalkylammonium hydroxides or alkali metal silicates, phosphates, hydroxides or carbonates. If necessary, relatively small mounts of wetting agents and/or organic solvents may be added to the solutions. Typical organic solvents which can be added in small amounts to the developer liquids are, for example, cyclohexanone, 2-ethoxyethanol, toluene, acetone and mixtures of these.

Photocuring is of great importance for printing inks, since the drying time of the binder is a crucial factor for the rate of production of graphic products and should be in the order of fractions of seconds. UV-curable inks are of particular importance for screen printing.

The mixtures according to the invention are, as mentioned above, also highly suitable for the production of printing plates. In this case, for example, mixtures of soluble linear polyamides or styrene-butadiene or styrene-isoprene rubber, polyacrylates or polymethyl methacrylates containing carboxyl groups, polyvinyl alcohols or urethane acrylates with photopolymerisable monomers, for example acrylamides, methacrylamides, acrylates or methacrylates, and a photoinitiator, are used. Films and plates produced from these systems (wet or dry) are exposed via the negative (or positive) of the print master, and the uncured parts are subsequently eluted with a suitable solvent.

A further area of application of photocuring is in metal coating, for example in the coating of sheeting and tubes, cans or bottle caps, and the photocuring of plastic coatings, for example of PVC-based floor or wall coverings.

Examples of the photocuring of paper coatings are the colourless lacquering of labels, record sleeves or book covers.

Another important use of photocurable compositions is for imaging processes aand for the optical production of information carriers. In this case, as described above, the layer applied to the carrier (wet or dry) is irradiated through a photomask with UV or visible light, and the unexposed areas of the layer are removed by treatment with a solvent (=developer). The photocurable layer can also be applied to metal by electrodeposition. The exposed areas are crosslinked/polymeric and thus insoluble and remain on the carrier. If appropriately stained, visible images are formed. If the carrier is a metallised layer, the metal in the unexposed areas can be removed by etching or increased in thickness by electroplating after exposing and developing. In this way, printed electronic circuits and photoresists can be produced.

The photosensitivity of the compositions according to the invention generally extends from the UV range (about 200 nm) to about 600 nm and thus covers a very broad range. Suitable radiation is present, for example, in sunlight or light from artificial light sources. The light sources used are therefore a large number of very varying types. Both point sources and large-area lamps (lamp carpets) are suitable. Examples are: carbon arc lamps, xenon arc lamps, mercury medium-pressure, high-pressure and low-pressure lamps, if desired doped with metal halides (metal halogen lamps), microwave-excited metal vapour lamps, excimer lamps, superactinic fluorescent tubes, fluorescent lamps, argon incandescent lamps, electronic flash lamps, photographic flood lamps, electron beams and X-rays, generated by synchrotrons or laser plasma. The distance between the lamp and the substrate to be coated according to the invention can vary, for example between 2 cm and 150 cm, depending on the application and the lamp type and power. Particularly suitable sources are laser light, e.g. excimer lasers, such as krypton F lasers, for exposure at 248 nm. It is also possible to employ lasers in the visible range. Here, the high sensitivity of the materials according to the invention is very advantageous. This method can be used to produce printed circuits in the electronics industry, lithographic offset printing plates or relief printing plates and photographic image-recording materials.

The invention also relates to the use of the above-described composition for the production of paints, printing inks, printing plates, dental compositions, resist materials and as an image-recording material, in particular for holographic recordings.

The invention likewise relates to a coated substrate which has been coated on at least one surface with a composition as described above, and to a process for the photographic production of relief images, in which a coated substrate is exposed imagewise, and the unexposed areas are then removed using a solvent.

The invention therefore also relates to a process for the photopolymerisation of nonvolatile, monomeric, oligomeric or polymeric compounds containing at least one ethylenically unsaturated double bond, wherein a compound of the formula I or II is added to the above-mentioned compounds and irradiated with light in the range from 200 to 600 nm.

The examples below illustrate the invention in greater detail. Parts and percentages, as in the remainder of the description and in the claims, are by weight, unless stated otherwise.

I) Preparation of the Starting Materials

EXAMPLE 1

Preparation of 2,4-dibenzyloxy-6-chloropyrimidine

The reaction is carried out under an argon protective-gas atmosphere. 24.8 ml (0.24 mol) of absolute benzyl alcohol in 100 ml of THF are added dropwise at 25° C. to 9.6 g of NaH (0.24 mol, 60% suspension in paraffin) in 120 ml of tetrahydrofuran (THF). The reaction mixture is warmed at 50° C. for 0.5 hour, cooled and then added dropwise to a solution, cooled to 0° C., of 13.8 ml of 2,4,6-trichloropyrimidine in 100 ml of THF. The mixture is allowed to warm to 25° C. overnight, and is then poured into 200 ml of water. After extraction with toluene three times, the combined organic phases are washed with 100 ml of water, dried using MgSO$_4$, filtered and evaporated on a rotary evaporator. Filtration through silica gel (eluent ethyl acetate:hexane 1:1) gives 39.9 g (100% of theory) of the title product.

EXAMPLE 2

Preparation of 2,4-isopropoxy-6-chloropyrimidine

The reaction is carried out under an argon protective-gas atmosphere. 4.6 g of sodium in small pieces are refluxed for 4 hours with 180 ml of isopropanol. The mixture is cooled, giving a light precipitate, which is dissolved in 50 ml of THF. This solution is, after cooling to 0° C., added dropwise to a solution of 11.5 ml (0.1 mol) of 2,4,6-trichloropyrimidine in 20 ml of absolute isopropanol. A white material immediately precipitates. The reaction mixture is allowed to warm to 25° C. overnight. Thin-layer chromatography shows the absence of starting material. The solvents are removed on a rotary evaporator and the residue is taken up in 100 ml of toluene. The resultant suspension is treated twice with 100 ml of water, and the aqueous phases are extracted a number of times with 100 ml of toluene. The organic phases are combined and dried using MgSO$_4$. After filtration, the solvent is removed, giving 22.8 g of a residue (99.1%). Separation on SiO$_2$ (eluent diethyl ether:hexane 5:95) gives 18 g (78.3% of theory) of the pure title compound.

EXAMPLE 3

Preparation of 6-chloro-4-(3-methylbut-1-oxy)-2-phenylpyrimidine

The reaction is carried out under an argon protective-gas atmosphere. A solution of 6.7 g (60.5 mmol) of sodium t-amylate in 50 ml of 3-methylbutanol is added dropwise to a solution, cooled to 0° C., of 12.4 g of 4,6-dichloro-2-phenylpyrimidine in 50 ml of 3-methylbutanol. The reaction mixture is allowed to warm to 25° C. overnight. Thin-layer chromatography shows the absence of starting material. The reaction mixture is poured into 180 ml of water and extracted three times with 80 ml of ethyl acetate. Combined organic phases are washed with water, dried using MgSO$_4$ and filtered. Removal of the solvent gives 14.6 g (96% of theory) of the title compound.

Elementary analysis:

| calc.: | C: | 69.1% | found: | C: | 69.1% |
|---|---|---|---|---|---|
| | H: | 6.2% | | H: | 6.4% |
| | N: | 10.1% | | N: | 10.0% |
| | Cl: | 12.8% | | Cl: | 12.6% |

EXAMPLE 4

Preparation of 6-chloro-2,4-diethoxypyrimidine 7.35 g (0.32 mol) of sodium in small pieces are added under an argon protective-gas atmosphere to 100 ml of absolute ethanol. The suspension is kept under reflux until the sodium has dissolved. The solution is cooled and added dropwise at 0° C. to a solution of 18.4 ml (0.16 mol) of 2,4,6-trichloropyrimidine in 100 ml of ethanol. The temperature is slowly increased to 25° C., the ethanol is removed on a rotary evaporator, and 100 ml of water are added. The mixture is then extracted three times with 100 ml of toluene. The combined organic phases are washed twice with 100 ml of water in each case, dried over MgSO$_4$, filtered and evaporated, giving 32.5 g of crude product. Purification by SiO$_2$ flash chromatography with hexane as eluent gives 24.9 g (76.9% of theory).

Elementary analysis:

| calc.: | C: | 47.4% | found: | C: | 48.3% |
|---|---|---|---|---|---|
| | H: | 5.5% | | H: | 5.8% |
| | N: | 13.8% | | N: | 13.8% |
| | Cl: | 17.5% | | Cl: | 17.0% |

EXAMPLES 5–8

The compounds of Examples 5–8 are prepared analogously to compounds of Example 1 or 3 and are shown in Table 1 below.

TABLE 1

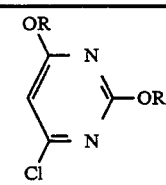

| Ex. | R | Synthesis | Yield [%] | Elemental analysis [%] atom/calculated/found | | |
|---|---|---|---|---|---|---|
| 5 | methoxy-ethyl | A | 48.3 | C:<br>H:<br>N: | 45.7<br>5.8<br>10.7 | 46.7<br>5.7<br>10.5 |
| 6 | 3-methyl-but-1-yl | C | 51.3 | C:<br>H:<br>N:<br>Cl: | 58.6<br>8.1<br>9.8<br>12.4 | 59.7<br>8.3<br>9.4<br>12.2 |
| 7 | cyclo-hexyl | A | 42.8 | C:<br>H:<br>N:<br>Cl: | 61.8<br>7.5<br>9.0<br>11.4 | 61.4<br>7.6<br>8.8<br>12.7 |
| 8 | cyclo-hexyl-methyl | A | 99.9 | C:<br>H:<br>N: | 63.8<br>8.0<br>8.3 | 64.2<br>8.3<br>8.1 |

TABLE 1-continued $$\text{structure: pyrimidine with OR at 4-position, OR at 2-position, Cl at 6-position}$$

| Ex. | R | Synthesis | Yield [%] | Elemental analysis [%] atom/calculated/found |
|---|---|---|---|---|
| | | | | Cl: 10.5 10.4 |

A: Method of Example 1
C: Method of Example 3

EXAMPLE 9

Preparation of 2,4-dichloro-6-(3-methylbut-1-oxy)pyrimidine

A solution of 28.6 g (0.26 mol) of sodium tert-amylate in 150 ml of 3-methylbutanol is stirred at 45°–50° C. for 30 minutes, cooled to 20° C. and added dropwise at −30° C. to a solution of 30 ml (0.26 mol) of trichloropyrimidine in 150 ml of 3-methylbutanol. When the solution has been added, the temperature is 0° C. The reaction mixture is left to stand overnight. The solvent is removed and the residue is taken up in 150 ml of water. Extraction three times with toluene, drying of the combined organic phases using MgSO₄ and evaporation give 60.36 g (98.7% of theory) of the title compound.

Elemental analysis:

| calc.: | C: | 46.0% | found: | C: | 45.9% |
|---|---|---|---|---|---|
| | H: | 9.1% | | H: | 9.1% |
| | N: | 11.9% | | N: | 12.0% |
| | Cl: | 30.2% | | Cl: | 30.6% |

EXAMPLE 10

Preparation of 6-chloro-2-isobutylthio-4-(3-methylbut-1-oxy)pyrimidine

A solution of 6.7 ml (55.3 mmol) of isobutyl mercaptan in 40 ml of THF is added dropwise to a suspension of 2.2 g of NaH in 90 ml of THF. During this addition, the temperature is prevented from rising above 50° C. by cooling. The solution is cooled to 20° C. and added to a solution of 13.0 g of 2,4-dichloro-6-(3-methylbut-1-oxy)pyrimidine in 80 ml of THF at −10° C. When the temperature has slowly risen to 25° C., the reaction mixture is poured into 200 ml of water. Extraction three times with toluene, drying of the combined organic phases using MgSO₄ and evaporation of the solvent give 17.3 g of a mixture. Separation on SiO₂ (petroleum ether 80°–110° C.) gives 11.5 g (71.9% of theory) of the title product.

Elemental analysis:

| calc.: | C: | 54.1% | found: | C: | 57.2% |
|---|---|---|---|---|---|
| | H: | 7.3% | | H: | 8.0% |
| | N: | 9.7% | | N: | 8.8% |
| | S: | 11.1% | | S: | 10.4% |
| | Cl: | 12.3% | | Cl: | 11.0% |

EXAMPLE 11

Preparation of 5-bromo-2,4-di(1,1-dimethylpropoxy)pyrimidine 11.1: 5-Bromouracil 39.4 g (0.35 mol) of uracil are dissolved in 200 ml of acetic acid, and the mixture is warmed to 70° C. The mixture is added dropwise over the course of 2 hours to a solution of 20 ml (0.38 mol) of bromine dissolved in 200 ml of acetic acid. The orange suspension is held at 70° C. overnight and then cooled to 0°–5° C. The precipitate obtained is filtered off, washed with 200 ml of cold water and dried, giving 60.2 g of 5-bromouracil (89.7% of theory).

Elemental analysis:

| calc.: | C: | 25.16% | found: | C: | 25.26% |
|---|---|---|---|---|---|
| | H: | 1.58% | | H: | 1.62% |
| | N: | 14.67% | | N: | 14.69% |
| | Br: | 41.84% | | Br: | 41.66% |

11.2: 5-Bromo-2,4-dichloropyrimidine ml of dimethylaniline and 40 g (0.21 mol) of 5-bromouracil are added at room temperature to 580 ml (6.3 mol) of phosphorus oxychloride, and the mixture is refluxed for 4.5 hours. The reaction mixture is slowly poured into ice water and extracted a number of times with dichloromethane. The combined organic phases are dried using MgSO₄, and filtered, and the solvent is evaporated on a rotary evaporator, giving 15 g (31.4% of theory) of 5-bromo-2,4-dichloropyrimidine.

Elemental analysis:

| calc.: | C: | 21.08% | found: | C: | 21.09% |
|---|---|---|---|---|---|
| | H: | 0.44% | | H: | 0.48% |
| | N: | 12.29% | | N: | 12.39% |
| | Cl: | 31.12% | | Cl: | 29.65% |
| | Br: | 35.07% | | Br: | 34.75% |

11.3: 5-Bromo-2,4-di(1,1-dimethylpropyloxy)-pyrimidine 21.5 g (0.195 mol) of sodium t-amylate are dissolved in 150 ml of THF under an argon protective gas, and 14.8 g (0.065 mol) of 5-bromo-2,4-dichloropyrimidine, dissolved in 80 ml of THF, are added. The reddish suspension is refluxed for 4 hours. The cooled reaction mixture is poured into 150 ml of water and extracted three times with toluene. Drying of the combined organic phases over MgSO₄ and removal of the solvent give 20.25 g of crude product. Purification on SiO₂ using ethyl acetate:petroleum ether as eluent in the ratio 5:95 gives 19.25 g (89.5% of theory) of the title compound.

Elemental analysis:

| calc.: | C: | 50.8% | found: | C: | 52.2% |
|---|---|---|---|---|---|
| | H: | 7.0% | | H: | 7.6% |
| | N: | 8.5% | | N: | 8.3% |
| | Br: | 24.1% | | Br: | 22.8% |

EXAMPLE 12

Preparation of 5-bromo-2,4,6-tris(3-methylbut-1-oxy)pyrimidine 12.1: 2,4,6-Tris(3-methylbut-1-oxy)pyrimidine 49.5 g (0.45 mol) of sodium t-amylate are dissolved in 200 ml of isopentanol at 50° C., and 13 ml (0.11 mol) of trichloropyrimidine in 50 ml of isopentanol are added dropwise to this solution over the course of 30 minutes. After the mixture has been warmed at 50° C. for one hour, thin-layer chromatography shows that the mixture no longer contains any starting material. The solvent is removed on a rotary evaporator, and the residue is poured into 200 ml of water. The mixture is extracted three times with 150 ml of toluene in each case, and the organic phases are dried using MgSO4 and filtered. Removal of the solvent gives 37.5 g (98.7% of theory) of 2,4,6-tris(3-methylbut-1-oxy)pyrimidine.

Elemental analysis:

| calc.: | | found: | |
|---|---|---|---|
| C: | 67.4% | C: | 67.3% |
| H: | 10.1% | H: | 10.6% |
| N: | 8.3% | N: | 7.6% |

12.2: 5-Bromo-2,4,6-tris(3-methylbut-1-oxy)pyrimydine 35.0 g (0.1 mol) of 2,4,6-tris(3-methylbut-1-oxy)-pyrimidine are dissolved in 75.7 ml of acetic acid and 14.7 ml of acetic anhydride, and the solution is warmed to 100° C. 23 g (0.13 mol) of N-bromosuccinimide are added, and the temperature of the reaction mixture is adjusted to 120° C. for 10 minutes and then held at 100° C. for 3 hours. After the mixture has been cooled, the solvent is removed on a rotary evaporator, 100 ml of water are added, and the suspension is extracted three times with 100 ml of dichloromethane. The combined organic phases are washed with water, dried using MgSO4 and filtered, and the solvent is removed on a rotary evaporator. Purification by SiO2 flash chromatography using special boiling point spirit (80°-110° C.) as eluent gives 33.6 g (77.9% of theory) of the title compound as a colourless liquid.

Elemental analysis:

| calc.: | | found: | |
|---|---|---|---|
| C: | 54.7% | C: | 56.8% |
| H: | 8.0% | H: | 8.5% |
| N: | 6.7% | N: | 6.2% |
| Br: | 19.1% | Br: | 17.7% |

EXAMPLE 13

Preparation of 5-bromo-2,4,6-tri(cyclohexyloxy)pyrimidine 20.3 ml (0.1925 mol) of cyclohexanol in 40 ml of THF are added dropwise under an argon protective gas to 5.8 g (0.1925 mol) of sodium hydride (60% in oil) in 100 ml of THF. When the addition is complete, the reaction mixture is heated at 50° C. for 40 minutes, and 6.3 ml (0.055 mol) of 2,4,6-trifluoropyrimidine in 40 ml of THF are added dropwise while the temperature is held at 50° C. The reaction mixture is cooled, poured into 180 ml of water and extracted three times with toluene. The combined organic phases are washed twice with 100 ml of water, dried over MgSO4 and filtered, and the solvent is removed on a rotary evaporator. Purification is carried out by medium-pressure chromatography on silica gel LiChroprep Si 60, particle size 25–40 μm, from MERCK, with toluene:hexane 1:1 as eluent.

Elemental analysis:

| calc.: | | found: | |
|---|---|---|---|
| C: | 70.6% | C: | 71.4% |
| H: | 9.2% | H: | 10.1% |
| N: | 7.5% | N: | 6.9% |

The bromination step is carried out as described under Example 12.2. The compound has a melting range of 120°–124° C.

EXAMPLES 14–18

The compounds of Examples 14–18 are prepared analogously to the compound of Example 13. In Examples 14 and 17, the THF is replaced by dimethylacetamide (DMA). The bromination step is carried out as described under Example 12.2. The compounds are listed in Table 2 below.

TABLE 2

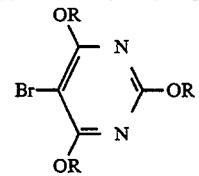

| Ex. | R | Melting range [°C.] | Elemental analysis [%] Atom/calculated/found | | |
|---|---|---|---|---|---|
| 14 | tetrahydrofurfuryl | 120–124 | C: | 49.7 | 50.3 |
| | | | H: | 5.9 | 6.2 |
| | | | N: | 6.1 | 5.9 |
| | | | Br: | 17.4 | 16.6 |
| 15 | isopropyl | oil | C: | 46.8 | 46.9 |
| | | | H: | 6.4 | 6.3 |
| | | | N: | 8.4 | 8.4 |
| | | | Br: | 24.0 | 24.3 |
| 16 | ethyl | 42–44 | C: | 41.3 | 41.4 |
| | | | H: | 5.2 | 5.2 |
| | | | N: | 9.6 | 9.6 |
| | | | Br: | 27.5 | 27.2 |
| 17 | methoxyethyl | oil | C: | 41.0 | 41.4 |
| | | | H: | 5.6 | 5.7 |
| | | | N: | 7.4 | 7.4 |
| | | | Br: | 21.0 | 19.8 |
| 18 | cyclohexylmethyl | 76–81 | C: | 60.6 | 61.1 |
| | | | H: | 7.9 | 8.6 |
| | | | N: | 5.7 | 5.4 |
| | | | Br: | 16.1 | 15.5 |

EXAMPLE 19

Preparation of 2,4,6-trimethoxypyrimidine 13.5 ml of 2,4,6-trichloropyrimidine in 80 ml of methanol are added dropwise, with cooling and under an argon protective gas to 106 ml of a 5.4M solution of sodium methoxide in methanol (0.576 mol). After the mixture has been refluxed for 90 minutes, the solvent is removed and the residue is poured into water. The mixture is extracted twice with toluene, the organic phases are dried using MgSO4 and filtered, and the solvent is removed. The target product is obtained in quantitative yield. NMR data: signals at 3.95 ppm (singlet for 9H) and 5.7 ppm (singlet for 1H). The bromination step is carried out as described under Example 12.2. NMR data: signals at 4 ppm (singlet for 9H).

EXAMPLE 20

Preparation of 6-chloro-4-(3-methylbut-1-oxy)-2-propylpyrimidine

The compound of Example 20 is prepared analogously to the compound of Example 3, with the 4,6- dichloro-2-phenylpyrimidine being replaced by 4,6-dichloro-2-propylpyrimidine.

Elemental analysis:

| calc.: | | found: | |
|---|---|---|---|
| C: | 59.4% | C: | 60.2% |
| H: | 7.9% | H: | 8.2% |
| N: | 11.5% | N: | 11.3% |
| Cl: | 14.6% | Cl: | 13.7% |

EXAMPLE 21

Preparation of 6-chloro-4-(2-ethylhexyloxy)-2-propylpyrimidine

The compound of Example 21 is prepared analogously to the compound of Example 3, with 4,6-dichloro-2-phenylpyrimidine being replaced by 4,6-dichloro-2-propylpyrimidine and 3-methylbutanol by 2-ethylhexanol.

NMR data (in CDCl$_3$): signals at 6.6 ppm (singlet for 1H), 4.3 ppm (doublet for 2H), 3.8 ppm (doublet of doublets) and 0.7-2.2 ppm (multiplet for 20H).

EXAMPLE 22

Preparation of 6-chloro-4-(3-methylbut-1-oxy)-2-i-propylpyrimidine

The compound of Example 22 is prepared analogously to the compound of Example 3, with 4,6-dichloro-2-phenylpyrimidine being replaced by 4,6-dichloro-2-i-propylpyrimidine NMR data (in CDCl$_3$): signals at 6.5 ppm (singlet for 1H), 4.4 ppm (doublet for 2H), 3.1 ppm (septet for 1H), 1.0-2.2 ppm (multiplet for 2H), 1.3 ppm (doublet for 6H) and 1.0 ppm (doublet for 6H).

EXAMPLE 23

Preparation of 6-chloro-4-(2-ethylhexyloxy)-2-i-propylpyrimidine

The compound of Example 23 is prepared analogously to the compound of Example 3, with 4,6-dichloro-2-phenylpyrimidine being replaced by 4,6-dichloro-2-i-propylpyrimidine and 3-methylbutanol by 2-ethylhexanol.

NMR data (in CDCl$_3$): signals at 6.5 ppm (singlet for 1H), 4.3 ppm (doublet for 2H), 3.1 ppm (septet for 1H) and 0.7-2.1 ppm (multiplet for 21H).

EXAMPLE 24

Preparation of 6-chloro-4-(3-methylbut-1-oxy)-2-decylpyrimidine

The compound of Example 24 is prepared analogously to the compound of Example 3, with 4,6-dichloro-2-phenylpyrimidine being replaced by 4,6-dichloro-2-decylpyrimidine.

NMR data (in CDCl$_3$): signals at 6.5 ppm (singlet for 1H), 4.4 ppm (doublet for 2H), 2.8 ppm (triplet for 2H) and 0.7-2.1 ppm (multiplet for 28H).

EXAMPLE 25

Preparation of 6-chloro-4-(2-ethylhexyloxy)-2-decylpyrimidine

The compound of Example 25 is prepared analogously to the compound of Example 3, with 4,6-dichloro-2-phenylpyrimidine being replaced by 4,6-dichloro-2-decylpyrimidine and 3-methylbutanol by 2-ethylhexanol.

NMR data (in CDCl$_3$): signals at 6.5 ppm (singlet for 1H), 4.3 ppm (doublet for 2H), 2.8 ppm (triplet for 2H) and 0.7-2.0 ppm (multiplet for 34H).

EXAMPLES 26-35

The compounds of Examples 26-35 are prepared analogously to the compounds of Examples 3, 4 or 43.3 using the respective alcohols or alkoxides. The results are shown in Table 3 below.

TABLE 3

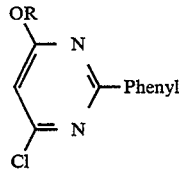

| Ex. | R | Melting range [°C.] | Elemental analysis [%] Atom/calculated/found | | | Preparation method |
|---|---|---|---|---|---|---|
| 26 | methyl | 66–71 | C: | 62.3 | 62.1 | D |
| | | | H: | 4.2 | 4.5 | |
| | | | N: | 9.1 | 8.6 | |
| | | | Cl: | 11.5 | 11.0 | |
| 27 | ethyl | 52–69 | C: | 63.3 | 63.2 | Z |
| | | | H: | 4.7 | 4.6 | |
| | | | N: | 8.7 | 8.3 | |
| | | | Cl: | 11.0 | 11.0 | |
| 28 | i-propyl | 57–64 | C: | 62.8 | 62.8 | C |
| | | | H: | 5.3 | 5.3 | |
| | | | N: | 11.3 | 11.1 | |
| | | | Cl: | 14.3 | 14.2 | |
| 29 | i-butyl | brown liquid | C: | 64.0 | 64.3 | C |
| | | | H: | 5.8 | 5.9 | |
| | | | N: | 10.7 | 10.5 | |
| | | | Cl: | 13.5 | 13.2 | |
| 30 | decyl | 40–45 | C: | 69.3 | 67.2 | C |
| | | | H: | 7.9 | 7.2 | |
| | | | N: | 8.1 | 8.5 | |
| | | | Cl: | 10.2 | 13.0 | |
| 31 | 2-ethyl- | yellow | C: | 68.1 | 67.8 | C |

TABLE 3-continued

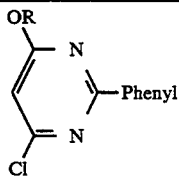

| Ex. | R | Melting range [°C.] | Elemental analysis [%] Atom/calculated/found | | | Preparation method |
|---|---|---|---|---|---|---|
|  | hexyl | oil | H: | 6.9 | 7.3 |  |
|  |  |  | N: | 8.8 | 8.7 |  |
| 32 | cyclohexyl | 44–48 | C: | 66.6 | 66.7 | Z |
|  |  |  | H: | 5.9 | 6.1 |  |
|  |  |  | N: | 9.7 | 8.9 |  |
|  |  |  | Cl: | 12.3 | 11.5 |  |
| 33 | cyclohexyl-methyl | 55–63 | C: | 67.4 | 66.4 | Z |
|  |  |  | H: | 6.3 | 6.1 |  |
|  |  |  | N: | 9.3 | 9.3 |  |
|  |  |  | Cl: | 11.7 | 13.1 |  |
| 34 | methoxyethyl | 43–46 | +) |  |  | C |
| 35 | phenoxyethyl | 123–127 | C: | 66.2 | 66.0 | Z |
|  |  |  | H: | 4.6 | 4.8 |  |
|  |  |  | N: | 8.6 | 8.5 |  |
|  |  |  | Cl: | 10.8 | 11.1 |  |

D: Preparation analogous to Example 4
C: Preparation analogous to Example 3
Z: Preparation analogous to Example 43.3
+): NMR data (CDCl₃): signals at 8.3 ppm (multiplet for 2H), 7.4 ppm (multiplet for 3H), 6.6 ppm (singlet for 1H), 4.6 ppm (multiplet for 2H), 3.7 ppm (multiplet for 2H) and 3.4 ppm (singlet for 3H).

EXAMPLE 36

Preparation of 6-chloro-2-p-chlorophenyl-4-(2-ethylhexyloxy)pyrimidine 36.1 p-Chlorobenzamidine hydrochloride
(cf. F. C. Schaefer und A. P. Krapcho, Journal of the Chemical Society, Vol. 27, (1962), 1255)

275.14 g (2 mol) of 4-chlorobenzonitrile, 427.9 g of ammonium chloride (8 mol) and 681.2 g (40 mol) of ammonia are introduced into a 6.3 l autoclave. Pressure rises to about 10 bar. The mixture is heated at 125° C. for 18 hours, during which the pressure rises to 65 bar. The solid residue is dissolved in 2 l of hot water and filtered while warm, the water phase is rendered basic by means of 30% NaOH. The resultant suspension is filtered, giving 240.8 g (63.1% of theory) of the product, having a melting point of 158.4°–158.5° C.

Elemental analysis:

| calc.: | C: | 54.4% | found: | C: | 54.2% |
|---|---|---|---|---|---|
|  | H: | 4.6% |  | H: | 4.6% |
|  | N: | 18.1% |  | N: | 17.7% |
|  | Cl: | 22.9% |  | Cl: | 22.9% |

36.2: 2-p-Chlorophenylhydroxypyrimidone 500 ml of methanol and 280.9 g (1.56 mol) of a 30% solution of sodium methoxide in methanol are mixed in a 2.5 l sulfonation flask under a protective-gas atmosphere. 120.4 g (0.78 mol) of p-chlorobenzamidine hydrochloride are added, and the mixture is refluxed for 30 minutes. 89.4 ml (103.05 g, 0.78 mol) of dimethyl malonate are then added dropwise over a period of 1.5 hours. The reaction mixture is allowed to react for a further hour and is then cooled, and the solvent is removed on a rotary evaporator. The residue is suspended in 2 l of water and acidified to a pH of 3–4 using acetic acid. The suspension is filtered, and the filter cake is washed with water and then dried, giving 169.4 g (97.6% of theory) of the product, with a melting point of above 250° C.

Elemental analysis:

| calc.: | C: | 54.0% | found: | C: | 53.4% |
|---|---|---|---|---|---|
|  | H: | 3.2% |  | H: | 3.3% |
|  | N: | 12.6% |  | N: | 12.2% |
|  | Cl: | 15.9% |  | Cl: | 15.8% |

36.3: 2-p-Chlorophenyl-4,6-dichloropyrimidine 90 g (0.4 mol) of 2-p-chlorophenylhydroxypyrimidone and 1 l of chlorobenzene are warmed to 50° C. in a 2.5 l sulfonation flask under a protective-gas atmosphere. 219.7 ml of phosphorus oxychloride (2.4 mol) are added dropwise over the course of about 3 hours at such a rate that the temperature remains at 50° C. 256 ml (1.6 mol) of dimethylaniline are then added dropwise over the course of about 1 hour, during which the temperature is again held at 50° C. The mixture is then warmed at 130° C. for about 16 hours and cooled, 2 l of ice water are added, the phases are separated and the aqueous phase is extracted with chlorobenzene. The combined organic phases are dried over MgSO₄, filtered and evaporated on a rotary evaporator. The residue is recrystallized from methanol, giving 42.8 g (51.5% of theory) of the product, having a melting point of 124.0°–124.1° C.

Elemental analysis:

| calc.: | C: | 46.3% | found: | C: | 46.3% |
|---|---|---|---|---|---|
|  | H: | 1.9% |  | H: | 2.1% |
|  | N: | 10.8% |  | N: | 10.6% |
|  | Cl: | 41.0% |  | Cl: | 40.3% |

36.4: 6-Chloro-2-(p-chlorophenyl)-4-(2-ethylhexyloxy)pyrimidine

The conversion of 2-(p-chlorophenyl)-4,6-dichloropyrimidine to 6-chloro-2-(p-chlorophenyl)-4-(2-ethylhexyloxy)pyrimidine is carried out analogously to the method described in Example 3, with 4,6-dichloro-2-phenylpyrimidine being replaced by 4,6-dichloro-2-(p-chlorophenyl)pyrimidine and 3-methylbutanol by 2-ethylhexanol.
Elemental analysis:

| calc.: | C: | 61.2% | found: | C: | 62.7% |
|---|---|---|---|---|---|
|  | H: | 6.3% |  | H: | 6.7% |
|  | N: | 7.9% |  | N: | 7.2% |
|  | Cl: | 20.1% |  | Cl: | 18.9% |

EXAMPLE 37

Preparation of 6-chloro-2-(p-chlorophenyl)-4-phenoxyethoxypyrimidine

The compound of Example 37 is prepared analogously to the compound of Example 36, but the reaction of the 4,6-dichloro starting material is not carried out by the method of Example 3, but instead by the method of Example 43.3.

EXAMPLE 38

Preparation of 4-chloro-6-(3-methylbut-1-oxy)-2-(p-octylphenylthio)-pyrimidine 38.1: p-Octylthiobenzonitrile 103.2 g (0.75 mol) of p-chlorobenzonitrile, 140 g of potassium carbonate and 143.2 ml (0.825 mol) of octanethiol in dimethylacetamide are stirred at 100° C. for about 16 hours in a sulfonation flask under a protective-gas atmosphere. The white suspension obtained is cooled, poured into ice water and extracted a number of times with dichloromethane. The organic phases are combined, washed with water, dried over MgSO4, filtered and evaporated, giving 193.1 g of crude product, which is distilled at 92° C./0.1 mm Hg.

38.2: 2-(p-Octylphenylthio)hydroxypyrimidone (without isolation of the amidine intermediate)

100 g (0.404 mol) of 4-octylthiobenzonitrile are dissolved in 300 ml of xylene in a 2.5 l sulfonation flask, and 41 g (0.525 mol) of a 50% suspension of sodium amide in toluene are added. The suspension is heated to 135° C. After 3.5 hours, the starting materials have reacted fully (check: thin-layer chromatography). The reaction mixture is cooled to 60° C., and 200 ml of methanol are slowly added dropwise. 46.3 ml (0.404 mol) of dimethyl malonate in 100 ml of methanol are added dropwise to the beige mixture at 60° C. over the course of one hour. The suspension, which is difficult to stir, is diluted with 200 ml of methanol and left to stand at room temperature for about 16 hours. The pH is then adjusted to 3 using acetic acid, and the viscous mixture is filtered. The solid residue is washed with water and dried at 40° C., giving 68.5% of theory of the product having a melting point of >250° C.
Elemental analysis:

| calc.: | C: | 65.0% | found: | C: | 64.7% |
|---|---|---|---|---|---|
|  | H: | 7.3% |  | H: | 7.1% |
|  | N: | 8.4% |  | N: | 8.0% |
|  | S: | 9.6% |  | S: | 9.6% |

38.3: 4,6-Dichloro-2-(p-octylphenylthio)pyrimidine 4,6-Dichloro-2-(p-octylphenylthio)pyrimidine is obtained analogously to the compound of Example 36.3 in a yield of 97.1% from 2-(p-octylphenylthio)hydroxypyrimidone.
Elemental analysis:

| calc.: | C: | 58.5% | found: | C: | 58.6% |
|---|---|---|---|---|---|
|  | H: | 6.0% |  | H: | 6.1% |
|  | N: | 7.6% |  | N: | 7.7% |
|  | S: | 8.7% |  | S: | 9.0% |
|  | Cl: | 19.2% |  | Cl: | 18.0% |

38.4: 4-Chloro-6-(3-methylbut-1-oxy)-2-(p-octylphenylthio)pyrimidine

The title product is obtained by the preparation method of Example 3 from 4,6-dichloro-2-(p-octylphenylthio)pyrimidine.
Elemental analysis:

| calc.: | C: | 65.6% | found: | C: | 65.8% |
|---|---|---|---|---|---|
|  | H: | 7.9% |  | H: | 8.0% |
|  | N: | 6.7% |  | N: | 6.6% |
|  | S: | 7.6% |  | S: | 7.7% |
|  | Cl: | 8.4% |  | Cl: | 8.4% |

EXAMPLES 39 and 40

The compounds of Examples 39 and 40 are obtained analogously to the preparation methods shown in Table 4 below from 4,6-dichloro-2-(p-octylphenylthio)pyrimidine.

TABLE 4

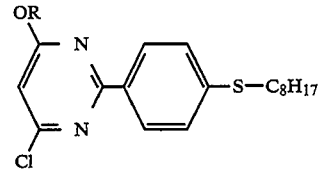

| Example | R | Elemental analysis [%] Atom/calc./found | | |
|---|---|---|---|---|
| 39 | ethyl | C: | 63.4 | 62.8 |
|  |  | H: | 7.2 | 7.2 |
|  |  | N: | 7.4 | 7.3 |
|  |  | S: | 8.5 | 8.6 |
|  |  | Cl: | 9.4 | 9.4 |
| 40 | phenoxy-ethyl | C: | 66.3 | 66.1 |
|  |  | H: | 6.6 | 6.6 |
|  |  | N: | 6.0 | 5.8 |
|  |  | S: | 6.8 | 6.8 |
|  |  | Cl: | 7.5 | 6.7 |

EXAMPLE 41

2-Butoxyphenyl-4-chloro-6-(3-methylbut-1-oxy)pyrimidine 41.1: p-Butoxybenzonitrile 250 ml of butanol and 15.2 g (0.66 mol) of sodium are heated in a sulfonation flask under a protective-gas atmosphere until the metal has fully reacted. The mixture is cooled, p-chlorobenzonitrile is added in portions, and the reaction mixture is subsequently refluxed for about 16 hours. The cooled mixture is poured into water and extracted with ethyl acetate. The organic phase is then dried using MgSO4 and filtered, and the solvent is evaporated, giving 95% of theory of the title product.
Elemental analysis:

| calc.: | C: | 75.4% | found: | C: | 75.4% |
|---|---|---|---|---|---|

|       |    |      |    |      |
|-------|----|------|----|------|
| -continued | | | | |
|       | H: | 7.4% | H: | 7.5% |
|       | N: | 8.8% | N: | 8.1% |

41.2: 2-(p-Butoxyphenyl)hydroxypyrimidone

The title product is obtained analogously to the compound of Example 38.2 in a yield of 83.3% of theory from p-butoxybenzonitrile. The product melts at 259°–265° C.

Elemental analysis:

| calc.: | C: | 64.6% | found: | C: | 64.5% |
|--------|----|-------|--------|----|-------|
|        | H: | 6.2%  |        | H: | 6.2%  |
|        | N: | 10.8% |        | N: | 10.6% |

41.3 2-(p-Butoxyphenyl)-4,6-dichloropyrimidine

The title product is obtained analogously to the compound of Example 38.3 in a yield of 46% of theory from 2-(p-butoxyphenyl)hydroxypyrimidone. The product melts at 54°–58° C.

Elemental analysis:

| calc.: | C:  | 56.6% | found: | C:  | 56.6% |
|--------|-----|-------|--------|-----|-------|
|        | H:  | 4.8%  |        | H:  | 4.9%  |
|        | N:  | 9.4%  |        | N:  | 9.4%  |
|        | Cl: | 23.9% |        | Cl: | 23.8% |

41.4: 2-Butoxyphenyl-4-chloro-6-(3-methylbut-1-oxy)pyrimidine

The preparation of 2-butoxyphenyl-4-chloro-6-(3-methylbut-1-oxy)pyrimidine is carried out by the method of Example 3 from 2-(p-butoxyphenyl)-4,6-dichloropyrimidine. The product is obtained in a yield of 87% of theory and has a melting range of 47°–50° C.

Elemental analysis:

| calc.: | C:  | 65.4% | found: | C:  | 65.6% |
|--------|-----|-------|--------|-----|-------|
|        | H:  | 7.2%  |        | H:  | 7.3%  |
|        | N:  | 8.0%  |        | N:  | 7.7%  |
|        | Cl: | 10.2% |        | Cl: | 9.9%  |

EXAMPLE 42

Preparation of 2-butoxyphenyl-4-chloro-6-(2-ethylhexyloxy)pyrimidine

The preparation is carried out by the method of Example 43.3 from 2-(p-butoxyphenyl)-4,6-dichloropyrimidine. The product is obtained in a yield of 96.8% of theory.

Elemental analysis:

| calc.: | C:  | 67.6% | found: | C:  | 67.5% |
|--------|-----|-------|--------|-----|-------|
|        | H:  | 8.0%  |        | H:  | 7.9%  |
|        | N:  | 7.2%  |        | N:  | 7.3%  |
|        | Cl: | 9.1%  |        | Cl: | 9.4%  |

EXAMPLE 43

Preparation of 4-chloro-2-(p-methylphenylthio)-6-phenoxyethoxypyrimidine

43.1: 2-(p-Methylphenylthio)hydroxypyrimidone

The title compound is obtained by reacting 6-(methylthio)benzonitrile with sodium amide giving the corresponding amide and reacting the latter, without prior isolation, with dimethyl malonate by the method described in Example 38.2. The product, having a melting point of >250° C., is obtained in a yield of 63.3% of theory.

Elemental analysis:

| calc.: | C:  | 56.4% | found: | C:  | 55.5% |
|--------|-----|-------|--------|-----|-------|
|        | H:  | 4.3%  |        | H:  | 4.4%  |
|        | N:  | 12.0% |        | N:  | 11.5% |
|        | Cl: | 13.7% |        | Cl: | 13.2% |

43.2: 4,6-Dichloro-2-(p-methylphenylthio)pyrimidine

The title compound is obtained by reacting the pyrimidone described under 43.1 by the method described under 38.3. The yield is 74.2% of theory, and the melting point, after recrystallisation, is 111.6°–113.4° C.

Elemental analysis:

| calc.: | C:  | 48.7% | found: | C:  | 48.7% |
|--------|-----|-------|--------|-----|-------|
|        | H:  | 3.0%  |        | H:  | 3.1%  |
|        | N:  | 10.3% |        | N:  | 10.6% |
|        | S:  | 11.8% |        | S:  | 12.0% |
|        | Cl: | 26.2% |        | Cl: | 25.8% |

43.3: 4-Chloro-2-(p-methylphenylthio)-6-phenoxyethoxypyrimidine 150 ml of 2-methyl-2-butanol, 2.33 g (0.101 mol) of sodium, 13 ml of 2-phenoxyethanol and a trace of iron(III) chloride are refluxed in a sulfonation flask. The suspension is refluxed until the sodium has fully reacted. This mixture is cooled, transferred into a dropping funnel under argon, and added dropwise at 0° C. over the course of 1.5 hours to a mixture of 25 g of 4,6-dichloro-2-(p-methylphenylthio)pyrimidine in 150 ml of absolute tetrahydrofuran. The reaction mixture is left to warm to 20° C. over the course of about 16 hours. The mixture is then poured into ice water and extracted a number of times with toluene. The organic phases are combined, washed with water, dried over MgSO$_4$, filtered and evaporated, giving 65% of theory of the title product having a melting range of 128°–132° C.

Elemental analysis:

| calc.: | C:  | 61.2% | found: | C:  | 61.0% |
|--------|-----|-------|--------|-----|-------|
|        | H:  | 4.6%  |        | H:  | 4.6%  |
|        | N:  | 7.5%  |        | N:  | 7.4%  |
|        | S:  | 8.6%  |        | S:  | 8.7%  |
|        | Cl: | 9.5%  |        | Cl: | 9.8%  |

EXAMPLE 44

Preparation of 4-chloro-6-ethoxy-2-(p-methylphenylthio)pyrimidine

The preparation is carried out analogously to the method described in Example 4; with 2,4,6-trichloropyrimidine being replaced by 4,6-dichloro-2-(p-methylphenylthio)pyrimidine. The title compound is obtained in a yield of 82% of theory and in a melting range of 94°–97° C.

Elemental analysis:

| calc.: | C: | 55.6% | found: | C: | 55.7% |
|--------|----|-------|--------|----|-------|
|        | H: | 4.7%  |        | H: | 4.7%  |
|        | N: | 10.0% |        | N: | 9.8%  |
|        | S: | 11.4% |        | S: | 11.4% |

-continued

| | | | |
|---|---|---|---|
| Cl: | 12.6% | Cl: | 12.6% |

EXAMPLE 45

Preparation of
4-chloro-2-(p-methylphenylthio)-6-(3-methylbut-1-oxy)pyrimidine

The preparation is carried out analogously to the method described in Example 3, with 4,6-dichloro-2-phenylpyrimidine being replaced by 4,6-dichloro-2-(p-methylphenylthio)pyrimidine. The title compound is obtained in a yield of 92.4% of theory and in a melting range of 83°–86° C.

NMR data (CDCl$_3$): signals at 8.3 ppm, 8.16 ppm, 7.3 ppm, 7.16 ppm (AA'BB' system 4H), 6.5 ppm (singlet, 1H), 4.5 ppm (triplet, 2H), 2.5 ppm (singlet, 3H), 1.7 ppm (triplet, 2H), 0.9 ppm (doublet, 6H).

EXAMPLE 46

Preparation of
4-chloro-2-(p-methylphenylthio)-6-(2-ethylhexyloxy)-pyrimidine

The preparation is carried out analogously to the method described in Example 3, with 4,6-dichloro-2-phenylpyrimidine being replaced by 4,6-dichloro-2-(p-methylphenylthio)pyrimidine and 3-methylbutanol by 2-ethylhexanol. The title compound is obtained as a resin in a yield of 85% of theory.

NMR data (CDCl$_3$): signals at 8.3 ppm, 8.1 ppm, 7.2 ppm, 7.1 ppm (AA'BB' system 4H), 6.5 ppm (singlet, 1H), 4.4 ppm (triplet, 2H), 2.5 ppm (singlet, 3H), 0.8–2.0 ppm (multiplet, 15H).

EXAMPLE 47

Preparation of
2-(biphenyl)-4-chloro-6-(3-methylbut-1-oxy)pyrimidine 47.1: 2-(Biphenyl)hydroxypyrimidone The preparation of the rifle compound is carried out analogously to the method described in Example 38.2, with the p-chlorobenzonitrile being replaced by p-phenylbenzonitrile. The product is obtained in a yield of 62% of theory, with a melting point of >250° C.

Elemental analysis:

| calc.: | C: | 72.2% | found: | C: | 71.6% |
|---|---|---|---|---|---|
| | H: | 4.6% | | H: | 4.6% |
| | N: | 10.6% | | N: | 10.0% |

47.2: 2-(Biphenyl)-4,6-dichloropyrimidine

The preparation of the rifle compound is carried out analogously to the method described in Example 38.3. The product is obtained in a yield of 62% of theory, with a melting point of 115.0°–115.4° C.

Elemental analysis:

| calc.: | C: | 63.8% | found: | C: | 63.9% |
|---|---|---|---|---|---|
| | H: | 3.3% | | H: | 3.6% |
| | N: | 9.3% | | N: | 8.8% |
| | Cl: | 23.5% | | Cl: | 22.6% |

47.3 2-(Biphenyl)-4-chloro-6-(3-methylbut-1-oxy)-pyrimidine

The preparation method and physical data of the title compound are shown in Table 5.

EXAMPLES 48 and 49:

The compounds of Example 48 and 49 and their physical data are shown in Table 5 below.

TABLE 5

| Example | R | Melting range [°C.] | Synthesis | Yield [%] | Elemental analysis [%] Atom/cacl./found | |
|---|---|---|---|---|---|---|
| 47.3 | 3-methyl-but-1-yl | 53–57 | Z | 57 | C: 71.5 H: 6.0 N: 7.9 Cl 10.1 | 71.5 6.0 7.7 9.8 |
| 48 | 2-ethyl-hexyl | resin | A | 80.3 | C: 72.8 H: 7.1 N: 7.1 Cl: 9.0 | 72.8 6.8 6.8 9.2 |
| 49 | phenoxy-ethyl | 123–127 | Z | 72 | C: 71.6 H: 4.8 N: 7.0 Cl: 8.8 | 71.3 4.7 6.9 8.3 |

A: Preparation analogous to Example 1
Z: Preparation analogous to Example 43.3

EXAMPLE 50

Preparation of
4-chloro-2-(p-phenylphenylthio)-6-(3-methylbut-1-oxy)pyrimidine 50.1: 2-(Phenylthiophenyl)benzonitrile The compound is prepared analogously to the method described in Example 38.1. The title compound obtained has a melting range of 110°–115° C.

50.2: 2-(Phenylthiophenyl)hydroxypyrimidone

The title compound is prepared analogously to the compound of Example 38.2. It is obtained in a yield of 63.8% of theory, with a melting point above 250° C.

Elemental analysis:

| calc.: | C: | 64.9% | found: | C: | 64.5% |
|---|---|---|---|---|---|
| | H: | 4.1% | | H: | 4.2% |
| | N: | 9.5% | | N: | 9.2% |
| | S: | 10.8% | | S: | 10.8% |

50.3: 4,6-Dichloro-2-(p-phenylthiophenyl)pyrimidine

The title compound is prepared analogously to the compound of Example 38.3. It is obtained in a yield of 91.9% of theory, with a melting range of 94°–97° C.

Elemental analysis:

| calc.: | C: | 57.7% | found: | C: | 58.5% |
|---|---|---|---|---|---|
| | H: | 3.0% | | H: | 3.3% |
| | N: | 8.4% | | N: | 8.4% |
| | S: | 9.6% | | S: | 9.6% |
| | Cl: | 21.3% | | Cl: | 19.2% |

50.4: 4-Chloro-2-(p-phenylthiophenyl)-6-(3-methylbut-1-oxy)pyrimidine

The compound of Example 50.4 and the preparation method and physical data thereof are shown in Table 6.

EXAMPLES 51 and 52:

The starting materials for the compounds of Examples 51 and 52 are prepared analogously to the compounds of Examples 38.1–38.3. The reaction to give the final product is carried out by the method shown in Table 6 below.

TABLE 6

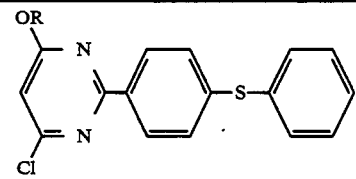

| Example | R | Melting range [°C.] | Yield [%] | Synthesis | Elemental analysis [%] Atom/calc./found | | |
|---|---|---|---|---|---|---|---|
| 50.4 | 3-methylbut-1-yl | 47–51 | 42 | Z | C: | 65.5 | 65.3 |
| | | | | | H: | 5.5 | 5.4 |
| | | | | | N: | 7.3 | 7.3 |
| | | | | | S: | 8.3 | 8.5 |
| | | | | | Cl: | 9.2 | 9.1 |
| 51 | 2-ethylhexyl | viscous liquid | 80 | Z | C: | 67.5 | 68.5 |
| | | | | | H: | 6.4 | 6.8 |
| | | | | | N: | 6.6 | 6.1 |
| | | | | | S: | 7.5 | 7.2 |
| | | | | | Cl: | 8.3 | 7.5 |
| 52 | phenoxyethyl | 101–105 | 54 | Z | C: | 66.3 | 66.2 |
| | | | | | H: | 4.4 | 4.5 |
| | | | | | N: | 6.4 | 6.3 |
| | | | | | S: | 7.4 | 7.5 |
| | | | | | Cl: | 8.2 | 7.7 |

Z: Preparation method analogous to Example 43.3

EXAMPLE 53

Preparation of 4-chloro-2-(p-dimethylaminophenyl)-6-(3-methylbut-1-oxy)pyrimidine

53.1: 2-(p-Dimethylaminophenyl)hydroxypyrimidinone

The title product is prepared analogously to the compound of Example 38.2 and in a yield of 84.1% of theory, with a melting point of above 250° C.

Elemental analysis:

| calc.: | C: | 62.3% | found: | C: | 56.9% |
|---|---|---|---|---|---|
| | H: | 5.7% | | H: | 6.1% |
| | N: | 18.2% | | N: | 16.4% |

53.2 2-(p-Dimethylaminophenyl)4,6-dichloropyrimidine

The compound is prepared analogously to the compound of Example 38.3. It is obtained in a yield of 63.8% of theory, with a melting range of 168.5°–169.5° C.

Elemental analysis:

| calc.: | C: | 53.8% | found: | C: | 54.6% |
|---|---|---|---|---|---|
| | H: | 4.1% | | H: | 4.3% |
| | N: | 15.7% | | N: | 15.7% |
| | Cl: | 26.4% | | Cl: | 25.2% |

53.3: 4-Chloro-2-(p-dimethylaminophenyl)-6-(3-methylbut-1-oxy)pyrimidine

The title product is prepared by the method of Example 43.3. It is obtained in a yield of 75.3% of theory, with a melting range of 83°–93° C.

Elemental analysis:

| calc.: | C: | 63.8% | found: | C: | 63.7% |
|---|---|---|---|---|---|
| | H: | 6.9% | | H: | 6.8% |
| | N: | 13.1% | | N: | 13.3% |
| | Cl: | 11.1% | | Cl: | 11.1% |

EXAMPLE 54

Preparation of 4-chloro-2-pyrrolo-6-(3-methylbut-1-oxy)pyrimidine

54.1: 4,6-Dichloro-2-pyrrolopyrimidine 19.7 g (0.12 mol) of 2-amino-4,6-dichloropyrimidine, 37 g (0.24 mol) of dimethoxytetrahydrofuran and 0.05 g of p-toluenesulfonic acid are heated to 140° C., and the methanol formed is immediately removed by distillation. The mixture is then stirred at 140° C. for 2 hours, cooled, diluted with dichloromethane and filtered through $SiO_2$, the solvent is removed, and the product is purified by column chromatography with hexane as eluent, giving 16.3 g, i.e. 63.2% of theory. After recrystallisation from methanol, the product has a melting point of 53.3°–56.3° C.

54.2: 4-Chloro-2-pyrrolo-6-(3-methylbut-1-oxy)pyrimidine

4-Chloro-2-pyrrolo-6-(3-methylbut-1-oxy)pyrimidine is prepared analogously to the method of Example 3 from 4,6-dichloro-2-pyrrolopyrimidine.

NMR data ($CDCl_3$): signals at 7.6 ppm (triplet, 2H), 6.4 ppm (singlet, 1H), 6.2 ppm (triplet, 2H), 4.4 ppm (triplet, 2H), 1.7 ppm (triplet, 3H) and 1.0 ppm (doublet, 6H).

EXAMPLE 55

Preparation of 4,6-di(3-methylbut-1-oxy)-2-phenylpyrimidine

The preparation is carried out analogously to the method described in Example 12.1, with the trichloropyrimidine being replaced by 4,6-dichloro-2-phenylpyrimidine. A yellow liquid is obtained in a yield of 89.3% of theory.

Elemental analysis:

| calc.: | C: | 73.1% | found: | C: | 73.1% |
|---|---|---|---|---|---|
| | H: | 8.6% | | H: | 8.6% |
| | N: | 8.5% | | N: | 8.6% |

EXAMPLE 56

Preparation of 5-bromo-4,6-di(3-methylbut-1-oxy)-2-phenylpyrimidine

The title product is obtained as a colourless liquid analogously to the method described in Example 12.2 in a yield of 72.4% of theory.

Elemental analysis:

| calc.: | C: | 59.0% | found: | C: | 59.4% |
|---|---|---|---|---|---|
| | H: | 6.7% | | H: | 6.7% |
| | N: | 6.9% | | N: | 6.8% |
| | Br: | 19.6% | | Br: | 19.3% |

EXAMPLE 57

Preparation of 6-chloro-4-(2-ethylhexyl) pyrimidine

The compound is prepared analogously to the method described in Example 3, with 4,6-dichloro-2-phenylpyrimidine being replaced by 4,6-dichloropyrimidine and 3-methylbutanol by 2-ethylhexanol. Yield: 76.2% of theory.

NMR data (CDCl$_3$): signals at 8.4 ppm (singlet, 1H), 6.7 ppm (singlet, 1H), 4.4 ppm (doublet, 2H) and 0.8–2.0 ppm (multiplet, 15H).

II) Preparation of the Titanocenes

EXAMPLE 58

Preparation of bis[cyclopentadienyl]bis[6-chloro-2,4-di(3-methylbut-1-oxy)pyrimidinyl]titanium 5.7 g (19.8 mmol) of 6-chloro-2,4-di(3-methylbut-1-oxy)pyrimidine in 40 ml of absolute tetrahydrofuran (THF) are cooled to −40° C. in a flask fitted with magnetic stirrer and argon inlet. 12.4 ml (19.8 mmol) of a 1.6M solution of n-butyllithium in hexane are added dropwise to this solution with stirring. 2.25 g (9 mmol) of solid dicyclopentadienyltitanium dichloride are added to the resultant orange solution at −40° C. The resultant suspension is allowed to warm slowly to 25° C. The mixture is then poured into 40 ml of water and filtered through ®Hyflo. The aqueous phase is separated off, and the red organic phase is dried using magnesium sulfate, filtered and evaporated on a rotary evaporator. The residue is purified by flash chromatography (SiO$_2$; eluent: ethyl acetate/special boiling point spirit [80°–110° C.] 5:95), giving 2.7 g (40% yield) of the title compound having a melting range of 89°–96° C.

Elemental analysis:

| calc.: | C: | 60.9% | found: | C: | 60.0% |
|---|---|---|---|---|---|
| | H: | 7.3% | | H: | 7.4% |
| | N: | 7.5% | | N: | 6.9% |
| | Cl: | 9.5% | | Cl: | 9.4% |

EXAMPLES 59–65

The compounds of Examples 60–66 are prepared analogously to the compound of Example 58. Their structures and physical data are shown in Table 7 below.

TABLE 7

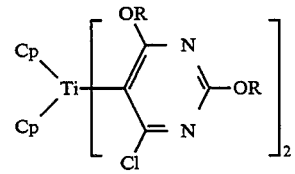

| Ex. | R | Melting range [°C.] | Yield [%] | Elemental analysis [%] Atom/calculated/found | | |
|---|---|---|---|---|---|---|
| 59 | methyl | 175–178 | — | — | | |
| 60 | ethyl | 140–150 | 55.2 | C: | 53.7 | 53.8 |
| | | | | H: | 5.5 | 5.0 |
| | | | | N: | 9.6 | 9.5 |
| | | | | Cl: | 12.2 | 12.0 |
| 61 | iso-propyl | 170–175 | 38.2 | C: | 56.5 | 56.6 |
| | | | | H: | 6.0 | 5.8 |
| | | | | N: | 8.8 | 8.1 |
| | | | | Cl: | 11.1 | 10.5 |
| 62 | methoxy-ethyl | — | 28.6 | C: | 51.4 | 50.9 |
| | | | | H: | 5.5 | 5.5 |
| | | | | N: | 8.0 | 8.2 |
| | | | | Cl: | 10.1 | 10.2 |
| 63 | cyclo-hexyl* | 89–96 | 13.9 | C: | 63.2 | 63.4 |
| | | | | H: | 6.8 | 7.1 |
| | | | | N: | 7.0 | 6.6 |
| | | | | Cl: | 8.9 | 8.9 |
| 64 | cyclo-hexyl-methyl | 164–172 | 49.0 | C: | 64.7 | 65.3 |
| | | | | H: | 7.3 | 7.9 |
| | | | | N: | 6.6 | 6.5 |
| | | | | Cl: | 8.3 | 7.8 |
| 65 | benzyl | 168–175 | 30.6 | C: | 66.6 | 65.9 |
| | | | | H: | 4.6 | 4.9 |
| | | | | N: | 6.8 | 6.1 |
| | | | | Cl: | 8.6 | 7.7 |

*The flash chromatography was carried out using ethyl acetate:hexane 20:80 as eluent

EXAMPLES 66 and 67

The compounds of Examples 66 and 67 are prepared analogously to the compound of Example 58, with the dicyclopentadienyltitanium dichloride being replaced by bis(methylcyclopentadienyl)titanium dichloride. The structures and physical data of the compounds are shown in Table 8.

TABLE 8

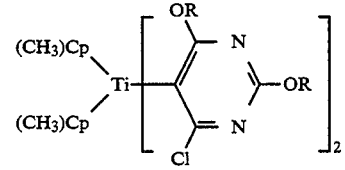

| Ex. | R | Melting range [°C.] | Yield [%] | Elemental analysis [%] Atom/calculated/found | | |
|---|---|---|---|---|---|---|
| 66 | methyl | 169–173 | — | C: | 55.2 | 55.5 |
| | | | | H: | 5.6 | 6.1 |
| | | | | N: | 9.2 | 8.4 |
| 67 | ethyl | 115–123 | 11 | C: | 57.4 | 56.4 |
| | | | | H: | 5.9 | 6.0 |
| | | | | N: | 10.3 | 10.1 |

EXAMPLE 68

Preparation of Chlorobis(cyclopentadienyl)(6-chloro-2,4-dicyclohexyloxypyrimidinyl)titanium 6.15 g (19.8 mmol) of 6-chloro-2,4-bis(cyclohexyloxy)pyrimidine are dissolved in 40 ml of THF under argon as protective gas, the solution is cooled to −40° C., and 12.4 ml of n-butyllithium (1.6M/hexane) are added dropwise. 2.25 g (9 mmol) of solid biscyclopentadienyltitanium dichloride are added to the resultant solution at −40° C. The reaction mixture is allowed to warm slowly from −40° C. to 25° C., is then poured into 40 ml of water and is filtered through ®Hyflo. The aqueous phase is separated off, and the organic phase is dried using magnesium sulfate, filtered and evaporated on a rotary evaporator. The residue is separated by flash chromatography (SiO$_2$), giving 1.0 g of the compound from Example 63 and 0.9 g of the title compound, having a melting range of 145°-155° C.

Elemental analysis:

| calc.: | C: | 59.7% | found: | C: | 60.3% |
|---|---|---|---|---|---|
| | H: | 6.2% | | H: | 6.2% |
| | N: | 5.4% | | N: | 6.9% |
| | Cl: | 13.6% | | Cl: | 13.1% |

EXAMPLE 69

Preparation of Bis[cyclopentadienyl]bis[6-chloro-2-i-butylthio-4-(3-methylbut-1-oxy)pyrimidinyl]titanium The compound of Example 69 is prepared analogously to the compound of Example 58, with 6-chloro-2,4-di(3-methylbut-1-oxy)pyrimidine being replaced by 6-chloro-2-i-butylthio-4-(3-methylbut-1-oxy)pyrimidine. The title compound is obtained with a melting range of 123°-132° C.

EXAMPLE 70

Preparation of Bis[cyclopentadienyl]bis[2,4-bis(1,1-dimethylpropoxy)pyrimidinyl]titanium The compound of Example 70 is prepared analogously to the compound of Example 58, with 6-chloro-2,4-di(3-methylbut-1-oxy)pyrimidine being replaced by 5-bromo-2,4-bis(1,1-dimethylpropoxy)pyrimidine. The compound obtained has a melting range of 135°-145° C.

EXAMPLES 71-78

The preparation of the compounds of Examples 71-78 is carried out analogously to that of the compound of Example 58, with the starting material used in each case being the 5-brominated pyrimidine derivative. The compounds of Examples 71-78 and their physical data are shown in Table 9.

TABLE 9

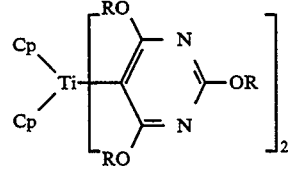

| Ex. | R | Melting range [°C.] | Yield [%] | Elemental analysis [%] Atom/calculated/found | | |
|---|---|---|---|---|---|---|
| 71 | methyl | 118-119 | 99.8 | C: | 55.8 | 55.7 |
| | | | | H: | 5.5 | 5.6 |
| | | | | N: | 10.9 | 11.0 |
| 72 | ethyl | 148-165 | 26.7 | C: | 60.0 | 59.8 |
| | | | | H: | 6.7 | 6.8 |
| | | | | N: | 9.3 | 9.2 |
| 73 | i-propyl | 135-145 | 44.2 | C: | 63.2 | 62.2 |
| | | | | H: | 7.7 | 7.6 |
| | | | | N: | 8.2 | 8.1 |
| 74 | methoxyethyl | liquid | 39.9 | C: | 55.4 | 55.6 |
| | | | | H: | 6.7 | 7.2 |
| | | | | N: | 7.2 | 6.8 |
| 75 | 3-methylbut-1-yl | liquid | 46.3 | C: | 67.6 | 68.7 |
| | | | | H: | 9.0 | 9.4 |
| | | | | N: | 6.6 | 5.9 |
| 76 | cyclohexyl | 75-85 | 13.5 | C: | 70.1 | 70.3 |
| | | | | H: | 8.3 | 8.9 |
| | | | | N: | 6.1 | 5.4 |
| 77 | cyclohexylmethyl | 127-138 | 42.9 | C: | 71.4 | 70.5 |
| | | | | H: | 8.8 | 8.9 |
| | | | | N: | 5.6 | 5.2 |
| 78 | tetrahydrofurfuryl | wax | 36.0 | C: | 61.5 | 60.7 |
| | | | | H: | 6.9 | 6.9 |
| | | | | N: | 6.0 | 5.7 |

EXAMPLE 79

Preparation of Biscyclopentadienylbis[6-chloro-4-(3-methylbut-1-oxy)-2-phenylpyrimidinyl]titanium The reaction is carried out under an argon protective-gas atmosphere. 8.6 ml of a 1.6M n-butyllithium solution in hexane (13.8 mmol) are added dropwise to a solution, cooled to 0° C., of 1.95 ml (13.8 ml) of diisopropylamine in 12.5 ml of THF. The resultant solution is cooled to −78° C., and a solution of 3.7 g of 4-chloro-6-(3-methylbut-1-oxy)-2-phenylpyrimidine in 12.5 ml of THF is added dropwise. When the mixture has been stirred at −78° C. for 2 hours, 1.1 g of solid biscyclopentadienyltitanium dichloride are added. The red suspension is stirred at −78° C. overnight, and excess carbon dioxide (solid) is added. The orange-brown solution is then poured into 90 ml of water and extracted with ethyl acetate. The organic phases are dried using MgSO$_4$, filtered and evaporated, giving 4.9 g of a red product. Purification on SiO$_2$ (ethyl acetate: special boiling point spirit [80°-110° C.] 1:9) gives 0.45 g of starting material, 0.3 g of an orange-red conformational isomer of the product, having a melting range of 66°-76° C., and 2.65 g of a yellow conformational isomer of the product, having a melting range of 169°-174° C.

Elemental analysis of the orange-red product:

| calc: | C: | 65.9% | found: | C: | 65.6% |
|---|---|---|---|---|---|
| | H: | 5.8% | | H: | 5.9% |
| | N: | 7.7% | | N: | 7.2% |
| | Cl: | 9.7% | | Cl: | 10.2% |

Elemental analysis of the yellow product:

| calc: | C: | 65.9% | found: | C: | 63.8% |
|---|---|---|---|---|---|
| | H: | 5.8% | | H: | 5.6% |
| | N: | 7.7% | | N: | 7.0% |
| | Cl: | 9.7% | | Cl: | 9.0% |

EXAMPLE 80

Selective Preparation of the Red Conformational Isomer of Biscyclopentadienylbis[6-chloro-4-(3-methylbut-1-oxy)-2-phenylpyrimidinyl]titanium A sulfonation flask is filled under an argon protective gas with 18 ml of distilled THF and 8.3 ml of diisopropylamine puriss., and the mixture is cooled to −78° C. 36.65 ml of a 1.6M solution of n-butyllithium in hexane are then added dropwise. The solution is stirred at 0° C. for 10 minutes. In a second reaction flask, 27 ml of absolute THF, 17.0 g of 4-chloro-6-(3-methylbut-1-oxy)-2-phenylpyrimidine and 6.95 g of biscyclopentadienyltitanium dichloride are brought into suspension by stirring (resultant suspension is red) and cooled to −20°/−15° C. The solution of the lithium diisopropylamine (LDA) is transferred into a dropping funnel and slowly added dropwise to the suspension. After half an hour, the cold solution is poured into a mixture of 60 ml of ethanol and 3.7 ml of acetic acid. The mixture is diluted with water and extracted a number of times with ethyl acetate. The combined organic phases are dried using MgSO4 and filtered, and the solvent is removed on a rotary evaporator. Flash column chromatography (eluent ethyl acetate:petroleum ether 20:80) gives 12.1 g, i.e. a yield of 60%, of the product having a melting range of 112°–122° C.

Elemental analysis:

| calc: | C: | 65.9% | found: | C: | 65.7% |
|---|---|---|---|---|---|
| | H: | 5.8% | | H: | 5.7% |
| | N: | 7.7% | | N: | 7.6% |
| | Cl: | 9.7% | | Cl: | 9.7% |

EXAMPLES 81–90

The compounds of Examples 81–90 are prepared analogously to the compound of Example 79. The compounds and their data are shown in Table 10 below.

TABLE 10

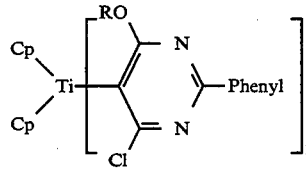

| Example | R | Melting range [°C.] | Yield [%] | | Elemental analysis [%] Atom/calc./found | |
|---|---|---|---|---|---|---|
| 81 | methyl | 185–200 | 53 | C: | 62.3 | 62.1 |
| | | | | H: | 4.2 | 4.5 |
| | | | | N: | 9.1 | 8.6 |
| | | | | Cl: | 11.5 | 11.0 |
| 82 | ethyl (A)* | 208–218 | 18 | C: | 63.3 | 63.2 |
| | | | | H: | 4.7 | 4.6 |
| | | | | N: | 8.7 | 8.3 |
| | | | | Cl: | 11.0 | 11.0 |
| | ethyl (B)* | 215–220 | 35 | C: | 63.3 | 63.0 |
| | | | | H: | 4.7 | 4.8 |
| | | | | N: | 8.7 | 8.2 |

TABLE 10-continued

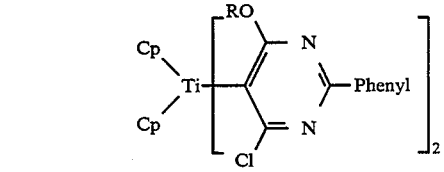

| Example | R | Melting range [°C.] | Yield [%] | | Elemental analysis [%] Atom/calc./found | |
|---|---|---|---|---|---|---|
| | | | | Cl: | 11.0 | 11.1 |
| 83 | i-propyl | 105–115 | 28 | C: | 64.2 | 65.2 |
| | | | | H: | 5.1 | 5.4 |
| | | | | N: | 8.3 | 7.8 |
| | | | | Cl: | 10.5 | 9.9 |
| 84 | i-butyl | 103–115 | 26.4 | C: | 65.1 | 65.5 |
| | | | | H: | 5.5 | 5.6 |
| | | | | N: | 8.0 | 7.5 |
| | | | | Cl: | 10.1 | 9.8 |
| 85 | decyl | 78–88 | 16.2 | C: | 69.0 | 68.3 |
| | | | | H: | 7.2 | 7.2 |
| | | | | N: | 6.4 | 6.3 |
| | | | | Cl: | 8.2 | 8.5 |
| 86 | 2-ethyl-hexyl | resin | 21.8 | C: | 67.9 | 67.9 |
| | | | | H: | 6.7 | 6.9 |
| | | | | N: | 6.9 | 6.6 |
| | | | | Cl: | 8.7 | 8.4 |
| 87 | cyclo-hexyl | 130–140 | 25 | C: | 66.9 | 67.6 |
| | | | | H: | 5.6 | 6.0 |
| | | | | N: | 7.4 | 7.0 |
| | | | | Cl: | 9.4 | 8.7 |
| 88 | cyclo-hexyl-methyl (A)* | 188–196 | 10 | C: | 67.6 | 67.4 |
| | | | | H: | 5.9 | 6.0 |
| | | | | N: | 7.2 | 7.0 |
| | | | | Cl: | 9.1 | 9.0 |
| | cyclo-hexyl-methyl (B)* | 85–95 | 15 | C: | 67.6 | 66.9 |
| | | | | H: | 5.9 | 5.9 |
| | | | | N: | 7.2 | 6.8 |
| | | | | Cl: | 9.1 | 10.0 |
| 89 | methoxy-ethyl | 94–104 | 42.2 | C: | 61.3 | 61.9 |
| | | | | H: | 4.9 | 5.2 |
| | | | | N: | 7.9 | 7.6 |
| | | | | Cl: | 10.1 | 9.8 |
| 90 | phenoxy-ethyl | 110–120 | 22.5 | C: | 66.6 | 65.0 |
| | | | | H: | 4.6 | 4.9 |
| | | | | N: | 6.8 | 6.1 |
| | | | | Cl: | 8.6 | 8.1 |

*(A) and (B) are two conformational isomers which can be separated by column chromatography

EXAMPLES 91–96

The compounds of Examples 91–96 are prepared analogously to the compound of Example 79. The compounds and their data are shown in Table 11 below. The substances are obtained as resins, with the exception of the compound of Example 91, which is a viscous liquid.

TABLE 11

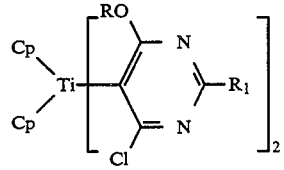

| Example | R | R1 | Yield [%] | | Elemental analysis [%] Atom/calc./found | |
|---|---|---|---|---|---|---|
| 91 | 3-methyl-but-1-yl | n-propyl | 40.6 | C: | 61.7 | 61.7 |
| | | | | H: | 7.0 | 7.1 |
| | | | | N: | 8.5 | 8.4 |
| | | | | Cl: | 10.7 | 10.0 |
| 92 | 2-ethyl- | n-propyl | 45 | C: | 64.4 | 64.9 |

TABLE 11-continued

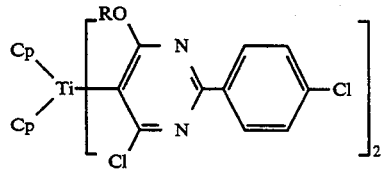

| Example | R | R₁ | Yield [%] | Elemental analysis [%] Atom/calc./found | |
|---|---|---|---|---|---|
| | hexyl | | | H: 7.8 | 8.3 |
| | | | | N: 7.5 | 6.9 |
| | | | | Cl: 9.5 | 8.5 |
| 93 | 3-methyl-but-1-yl | i-propyl | 6.2 | C: 61.7 | 59.8 |
| | | | | H: 7.0 | 6.6 |
| | | | | N: 8.5 | 7.8 |
| | | | | Cl: 10.7 | 10.0 |
| 94 | 2-ethyl-hexyl | i-propyl | 41.3 | C: 64.4 | 62.1 |
| | | | | H: 7.8 | 7.7 |
| | | | | N: 7.5 | 7.0 |
| | | | | Cl: 9.5 | 8.9 |
| 95 | 3-methyl-but-1-yl | decyl | 22 | C: 67.2 | 65.3 |
| | | | | H: 8.7 | 8.9 |
| | | | | N: 6.5 | 5.9 |
| | | | | Cl: 8.3 | 6.7 |
| 96 | 2-ethyl-hexyl | decyl | — | C: 68.8 | 68.5 |
| | | | | H: 9.2 | 10.0 |
| | | | | N: 6.0 | 4.8 |
| | | | | Cl: 7.5 | 5.9 |

EXAMPLES 97 and 98

The compounds of Examples 97 and 98 are prepared analogously to the compound of Example 79. The compounds and their data are shown in Table 12 below.

TABLE 12

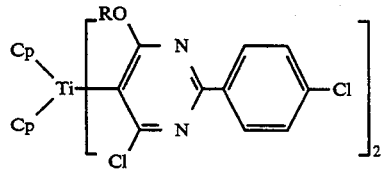

| Example | R | Melting range [°C.] | Yield [%] | Elemental analysis [%] Atom/calc./found | |
|---|---|---|---|---|---|
| 97 | 2-ethylhexyl | 83–95 | 42 | C: 62.6 | 62.8 |
| | | | | H: 5.9 | 6.1 |
| | | | | N: 6.4 | 5.9 |
| | | | | Cl: 16.1 | 15.7 |
| 98 | phenoxyethyl | 107–117 | 15.5 | C: 61.5 | 62.1 |
| | | | | H: 4.0 | 4.3 |
| | | | | N: 6.2 | 6.1 |
| | | | | Cl: 15.8 | 15.4 |

EXAMPLES 99 and 100

The compounds of Examples 99 and 100 are prepared analogously to the compound of Example 79. The compounds and their data are shown in Table 13 below.

TABLE 13

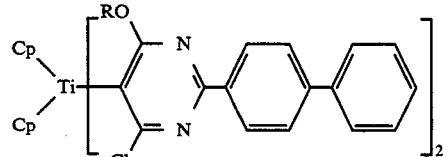

| Example | R | Melting range [°C.] | Yield [%] | Elemental analysis [%] Atom/calc./found | |
|---|---|---|---|---|---|
| 99 | 3-methyl-but-1-yl | 90–110 | 65 | C: 66.0 | 66.0 |
| | | | | H: 6.7 | 6.9 |
| | | | | N: 6.4 | 6.3 |
| | | | | Cl: 8.1 | 8.2 |
| 100 | 2-ethylhexyl | resin | 28.7 | C: 67.7 | 69.7 |
| | | | | H: 7.4 | 7.9 |
| | | | | N: 5.9 | 5.5 |
| | | | | Cl: 7.4 | 7.0 |

EXAMPLES 101–103

The compounds of Examples 101–103 are prepared analogously to the compound of Example 79. The compounds and their data are shown in Table 14 below.

TABLE 14

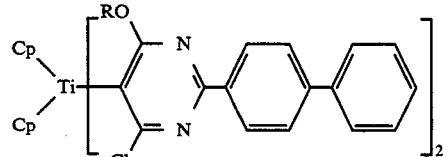

| Example | R | Melting range [°C.] | Yield [%] | Elemental analysis [%] Atom/calc./found | |
|---|---|---|---|---|---|
| 101 | 3-methyl-but-1-yl | 73–83 | 7.3 | C: 70.8 | 70.8 |
| | | | | H: 5.7 | 6.2 |
| | | | | N: 6.4 | 5.6 |
| | | | | Cl: 8.0 | 7.3 |
| 102 | 2-ethylhexyl | 73–85 | 33.5 | C: 72.0 | 72.1 |
| | | | | H: 6.7 | 6.8 |
| | | | | N: 5.8 | 5.2 |
| | | | | Cl: 7.3 | 7.0 |
| 103 | phenoxyethyl | 110–120 | 13 | C: 71.0 | 71.0 |
| | | | | H: 4.7 | 5.1 |
| | | | | N: 5.7 | 5.6 |
| | | | | Cl: 7.2 | 7.0 |

EXAMPLES 104–110

The compounds of Examples 104–110 are prepared analogously to the compound of Example 79. The compounds and their data are shown in Table 15 below.

TABLE 15

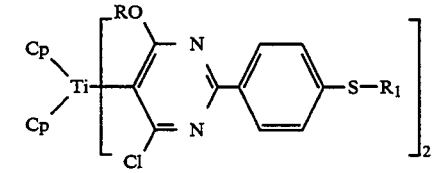

| Example | R | R₁ | Melting range [°C.] | Yield [%] | Elemental analysis [%] Atom/calc./found | |
|---|---|---|---|---|---|---|
| 104 | 3-methyl-but-1-yl | octyl | resin | 47.0 | C: 66.1 | 65.7 |
| | | | | | H: 7.3 | 7.2 |
| | | | | | N: 5.5 | 5.1 |
| | | | | | S: 6.3 | 6.1 |

TABLE 15-continued

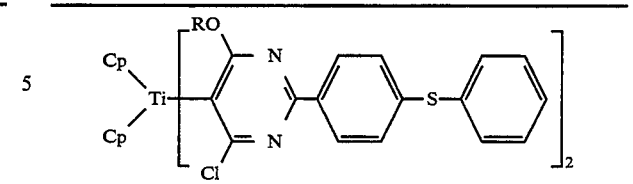

| Example | R | R₁ | Melting range [°C.] | Yield [%] | Elemental analysis [%] Atom/calc./found | | |
|---|---|---|---|---|---|---|---|
| 105 | ethyl | octyl | resin | 15.5 | Cl: | 7.0 | 7.4 |
| | | | | | C: | 64.3 | 64.7 |
| | | | | | H: | 6.7 | 6.9 |
| | | | | | N: | 6.0 | 5.5 |
| | | | | | S: | 6.9 | 6.3 |
| 106 | phenoxyethyl | octyl | resin | 40.4 | Cl: | 7.6 | 7.1 |
| | | | | | C: | 66.6 | 66.8 |
| | | | | | H: | 6.3 | 6.3 |
| | | | | | N: | 5.0 | 5.0 |
| | | | | | S: | 5.7 | 5.6 |
| 107 | ethyl | methyl | 155–165 | 44.6 | Cl: | 6.3 | 6.2 |
| | | | | | C: | 58.6 | 59.7 |
| | | | | | H: | 4.6 | 4.9 |
| | | | | | N: | 7.6 | 7.2 |
| | | | | | S: | 8.7 | 8.3 |
| 108 | 3-methyl-but-1-yl | methyl | 102–112 | 45.0 | Cl: | 9.6 | 9.1 |
| | | | | | C: | 61.4 | 61.4 |
| | | | | | H: | 5.7 | 5.8 |
| | | | | | N: | 6.8 | 6.6 |
| | | | | | S: | 8.6 | 8.7 |
| 109 | 2-ethyl-hexyl | methyl | resin | 24.6 | Cl: | 7.8 | 7.5 |
| | | | | | C: | 63.3 | 61.4 |
| | | | | | H: | 6.5 | 6.2 |
| | | | | | N: | 6.2 | 5.9 |
| | | | | | S: | 7.8 | 7.7 |
| 110 | phenoxyethyl | methyl | 101–110 | 15.0 | Cl: | 7.1 | 7.0 |
| | | | | | C: | 62.5 | 63.3 |
| | | | | | H: | 4.6 | 5.0 |
| | | | | | N: | 6.1 | 5.7 |
| | | | | | S: | 7.0 | 6.4 |

EXAMPLES 111–113

The compounds of Examples 111–113 are prepared analogously to the compound of Example 79. The compounds and their data are shown in Table 16 below.

TABLE 16

| Example | R | Melting range [°C.] | Yield [%] | Elemental analysis [%] Atom/calc./found | | |
|---|---|---|---|---|---|---|
| 111 | 3-methyl-but-1-yl | 87–97 | 20.8 | C: | 66.0 | 65.5 |
| | | | | H: | 5.3 | 5.3 |
| | | | | N: | 5.9 | 5.9 |
| | | | | S: | 7.5 | 7.5 |
| | | | | Cl: | 6.8 | 6.7 |
| 112 | 2-ethylhexyl | 67–77 | 44.6 | C: | 67.6 | 67.9 |
| | | | | H: | 6.1 | 6.3 |
| | | | | N: | 5.4 | 5.2 |
| | | | | S: | 6.2 | 6.3 |
| | | | | Cl: | 6.9 | 6.8 |
| 113 | phenoxyethyl | 94–104 | 32.7 | C: | 66.6 | 67.7 |
| | | | | H: | 4.4 | 4.9 |
| | | | | N: | 5.3 | 5.1 |
| | | | | S: | 6.8 | 6.5 |
| | | | | Cl: | 6.1 | 5.9 |

EXAMPLE 114

Preparation of Bis(cyclopentadienyl)bis[6-chloro-2-(p-N,N-dimethylaminophenyl)-4-(3-methylbut1-oxy)pyrimidinyl]-titanium The preparation of the title compound is carried out analogously to the method described in Example 79. The compound is obtained in a yield of 16% of theory, with a melting range of 105°–115° C.

Elemental analysis:

| calc: | C: | 64.8% | found: | C: | 64.7% |
|---|---|---|---|---|---|
| | H: | 6.4% | | H: | 6.5% |
| | N: | 10.3% | | N: | 10.7% |
| | Cl: | 8.7% | | Cl: | 8.8% |

EXAMPLE 115

Preparation of Bis(cyclopentadienyl)bis[6-chloro-4-(3-methylbut-1-oxy)-2-pyrrolopyrimidinyI]titanium The preparation of the tide compound is carried out analogously to the method described in Example 79. The compound is obtained in a yield of 38% of theory, with a melting range of 152°–158° C.

Elemental analysis:

| calc: | C: | 61.6% | found: | C: | 59.2% |
|---|---|---|---|---|---|
| | H: | 5.7% | | H: | 6.5% |
| | N: | 11.9% | | N: | 11.0% |
| | Cl: | 10.0% | | Cl: | 9.4% |

EXAMPLE 116

Preparation of Bis(cyclopentadienyl)bis[4,6-di(3-methylbut-1-oxy)-2-phenylpyrimidinyl]titanium The preparation of the title compound is carried out analogously to the method described in Example 79. The compound is obtained in a yield of 37% of theory, with a melting range of 173°–175° C.

Elemental analysis:

| calc: | C: | 72.1% | found: | C: | 72.3% |
|---|---|---|---|---|---|
| | H: | 7.7% | | H: | 7.8% |
| | N: | 6.7% | | N: | 6.6% |

EXAMPLE 117

Preparation of
Bis(cyclopentadienyl)bis[6-chloro-4-(2-ethylhexyloxy)-pyrimidinyl]titanium The preparation of the title compound is carried out analogously to the method described in Example 79. The compound is obtained as a resin in a yield of 49% of theory.

Elemental analysis:

| calc: | C: | 61.7% | found: | C: | 61.9% |
|---|---|---|---|---|---|
| | H: | 7.0% | | H: | 7.4% |
| | N: | 8.5% | | N: | 8.1% |
| | Cl: | 10.7% | | Cl: | 10.0% |

EXAMPLE 118

Preparation of
bis(cyclopentadienyl)-[4-chloro-6-(3-methylbut-1-oxy)-2-phenylpyrimidinyl]acetoxytitanium 69 ml (0.11 mol, 1.6M) of butyllithium are added dropwise over the course of 15 minutes under a nitrogen atmosphere to a solution of 15.6 ml (0.11 mol) of diisopropylamine in 200 ml of tetrahydrofuran at 0° C. This solution is added dropwise at from −70° to −60° C. over the course of 2 hours to a suspension of 24.9 g (0.1 mol) of titanocene dichloride and 27.7 g (0.1 mol) of 4-chloro-6-(3-methylbut-1-oxy)-2-phenylpyrimidine in 1000 ml of tetrahydrofuran. The reaction mixture is stirred at −70° C. for 1 hour, allowed to warm to room temperature over the course of about 3 hours and then poured, with stirring, into water and 19.0 g (0.23 mol) of acetic acid. The resultant red-orange emulsion is filtered through ®Hyflo. The organic phase is separated off, dried using magnesium sulfate, filtered and evaporated on a rotary evaporator. The residue is purified by flash chromatography with hexane:ethyl acetate in the ratio 3:1 as eluent, giving 11.2 g (22.4% of theory) of the title compound as a yellow powder having a melting point of 158° C.

Elemental analysis:

| calc: | C: | 62.4% | found: | C: | 62.9% |
|---|---|---|---|---|---|
| | H: | 5.8% | | H: | 5.8% |
| | N: | 5.6% | | N: | 4.6% |
| | Cl: | 7.1% | | Cl: | 7.0% |

EXAMPLE 119

Preparation of
bis(cyclopentadienyl)-[4-chloro-6-(3-methylbut-1-oxy)-2-phenylpyrimidinyl]benzoyloxytitanium The title compound is prepared analogously to the compound of Example 118, with the acetic acid being replaced by benzoic acid. 2.6 g (4.6% of theory) of the title compound are obtained as an orange powder having a melting point of 118°–120° C.

Elemental analysis:

| calc: | C: | 66.1% | found: | C: | 66.3% |
|---|---|---|---|---|---|
| | H: | 5.6% | | H: | 5.6% |
| | N: | 5.0% | | N: | 4.6% |
| | Cl: | 6.3% | | Cl: | 6.4% |

EXAMPLE 120

Preparation of
bis(cyclopentadienyl)bis[3,5-dichloro-1-phenylpyrazol-4-yl]titanium 120.1: N-Phenyl-3,5-dichloropyrazole The preparation of N-phenyl-3,5-dichloropyrazole is carried out by the method described by A. Michaelis and H. Röhmer in Berichte XXXIII, 3009 (1898). However, N-phenyl-3,5-dichloropyrazole is not obtained as a solid having a melting range of 22°–26° C., as described therein, but is obtained as a pale yellow oil.

Elemental analysis of N-phenyl-3,5-dichloropyrazole:

| calc: | C: | 50.8% | found: | C: | 50.8% |
|---|---|---|---|---|---|
| | H: | 2.8% | | H: | 3.0% |
| | N: | 13.2% | | N: | 13.3% |
| | Cl: | 33.3% | | Cl: | 32.9% |

120.2:
Bis(cyclopentadienyl)[4-chloro-6-(3-methylbut-1-oxy)-2-phenylpyrimidinyl]benzoyloxytitanium The title product is prepared analogously to the compound of Example 80. However, the 4-chloro-6-(3-methylbut-1-oxy)-2-phenylpyrimidine is replaced by N-phenyl-3,5-dichloropyrazole. The compound is also isolated by a different method: after the lithium diisopropylamine has been added, the reaction mixture is poured into water/acetic acid, giving a red precipitate. The precipitate is filtered, washed with water and dried, giving 80.4% of theory of the title compound having a melting range of 234°–244° C.

Elemental analysis:

| calc: | C: | 55.9% | found: | C: | 55.9% |
|---|---|---|---|---|---|
| | H: | 3.4% | | H: | 3.8% |
| | N: | 9.3% | | N: | 8.9% |
| | Cl: | 23.6% | | Cl: | 22.0% |

EXAMPLE 121

Reactivity Test in a Varnish

The following components are mixed to give a photocurable composition:
 10.0 g of dipentaerythritol monohydroxypentaacrylate, ®SR 399, Sartomer Co., Berkshire, GB
 15.0 g of tripropylene glycol diacrylate, Sartomer Co., Berkshire, GB
 15.0 g of N-vinylpyrrolidone, Fluka
 10.0 g of trismethylolpropane triacrylate, Degussa
 50.0 g urethane acrylate ®Acrilan AJ20, Societé National des Poudres et Explosifs
 0.3 g of flow assistant ®Byk 300, Byk-Mallinckrodt.

Portions of this composition are mixed with 0.3%, based on the solids content, of the titanocene photoinitiator according to the invention. All operations are carried out under a red light. The samples mixed with initiator are applied to a 200 μm aluminium foil. The dry layer thickness is 60 μm. A 76 μm thick polyester film is applied to this layer, and a standardised test negative having 21 steps of different optical density (Stauffer wedge) is laid thereon. The sample is covered by a second UV-transparent film and pressed against a metal plate by means of vacuum. The exposure is carried out in a first test series for 5 seconds, in a second test series for 10 seconds and in a third test series for 20 seconds at a distance of 30 cm by means of a 5 kW lamp. After the exposure, the film and the mask are removed, and the exposed layer is developed for 10 seconds in ethanol in an ultrasound bath at 23° C. The drying is carried out at 40° C. for 5 minutes in a fan-assisted oven. The sensitivity of the initiator system used is characterised by the indication of the final wedge step imaged tack-free. The higher the number of steps, the more sensitive the tested system.

The results are shown in Tables 17 and 18.

TABLE 17

| Compound from Ex. | Number of imaged steps | | | |
|---|---|---|---|---|
| | after 5s | 10s | 20s | exposure |
| 60 | 9 | 12 | 15 | |
| 61 | 8 | 11 | 13 | |
| 62 | 8 | 11 | 13 | |
| 65 | 7 | 10 | 13 | |
| 72 | 7 | 7 | 11 | |
| 74 | 8 | 11 | 13 | |
| 75 | 9 | 11 | 14 | |

TABLE 18

| Compound from Ex. | Number of imaged steps | | | |
|---|---|---|---|---|
| | after 5s | 10s | 20s | exposure |
| 58 | 8 | 10 | 13 | |
| 63 | 7 | 9 | 12 | |
| 68 | 7 | 9 | 12 | |
| 73 | 9 | 11 | 15 | |
| 76 | 7 | 9 | 12 | |

EXAMPLE 122

Reactivity Test in a Solder Resist

A composition is prepared from:
37.64 g of pentaerythritol triacrylate ®SR 444, Sartomer Co., Berkshire, GB
10.76 g of hexamethoxymethylmelamine ®Cymel 301, American Cyanamid Corp.
47.30 g of thermoplastic acrylate containing carboxyl groups ®Carboset 525, B.F. Goodrich, Ohio, USA
4.30 g of polyvinylpyrrolidone PVP 30, GAF AG, Zug, Switzerland.
To 100 g of this composition are added
0.5 g of Irgalith Green
319.0 g of methylene chloride and
30.0 g of methanol.

Portions of this composition are mixed with 0.3%, based on the solids content, of the titanocene compound to be tested. All operations are carried out under red light. The samples mixed with initiator are applied in a dry layer thickness of 30 μm to a 200 μm aluminium foil. The solvent is removed by warming at 60° C. for 15 minutes in a fan-assisted oven. A 76 μm thick polyester film is applied to the layer, and a standardised test negative having 21 steps of different optical density (Stauffer wedge) is placed thereon. The sample is covered by a second UV-transparent film and pressed against a metal plate by means of vacuum. The sample is then exposed by means of a 5 kW lamp in a first test series for 10 seconds, in a second test series for 20 seconds and in a third test series for 40 seconds at a distance of 30 cm. After the exposure, the films and the mask are removed, and the exposed layer is developed with developer A* for 4 minutes at 23° C. in an ultrasound bath and subsequently dried. The sensitivity of the initiator system used is characterised by the indication of the final wedge step imaged tack-free. The higher the number of steps, the more sensitive the system.

*Developer A comprises:
15.00 g of sodium metasilicate.9 H$_2$O
0.16 g of potassium hydroxide
3.00 g of polyethylene glycol 6000
0.50 g of levulinic acid
1000.0 g of demineralised water The results are shown in Tables 19 and 20.

TABLE 19

| Compound from Ex. | Number of imaged steps | | | |
|---|---|---|---|---|
| | after 10s | 20s | 40s | exposure |
| 61 | 8 | 11 | 13 | |
| 62 | 8 | 10 | 13 | |
| 65 | 7 | 9 | 12 | |

TABLE 20

| Compound from Ex. | Number of imaged steps | | | |
|---|---|---|---|---|
| | after 10s | 20s | 40s | exposure |
| 58 | 9 | 12 | 15 | |
| 60 | 9 | 12 | 15 | |
| 63 | 8 | 10 | 13 | |
| 64 | 8 | 10 | 13 | |
| 68 | 8 | 10 | 13 | |

EXAMPLE 123

Reactivity in an Etch Resist Formulation

The following components are mixed with a photocurable composition:
10.0 g of dipentaerythritol monohydroxypentaacrylate, ®SR 399, Sartomer Co., Berkshire, GB
15.0 g of tripropylene glycol diacrylate, Sartomer Co., Berkshire, GB
15.0 g of N-vinylpyrrolidone, Fluka
10.0 g of trimethylolpropane triacrylate, Degussa
50.0 g urethane acrylate ®Actilan AJ20, Societé National des Poudres et Explosifs
0.3 g of flow assistant ®Byk 300, Byk-Mallinckrodt.

Portions of this composition are mixed with 0.3%, based on the solids content, of the titanocene photoinitiator according to the invention. All operations are carried out under a red light. The samples mixed with initiator are applied in a thickness of 100 μm to a 300 μm aluminium foil. The dry layer thickness is 60 μm–70 μm. A 76 μm thick polyester film is applied to this layer, and a standardised test negative having 21 steps of different optical density (Stauffer wedge) is laid thereon. The sample is covered by a second UV-transparent polyester film and pressed against a metal plate by means of vacuum. The exposure is carried out in a first test series for 5 seconds, in a second test series for 10 seconds and in a third test series for 20 seconds at a distance of 30 cm by means of a 5 kW lamp. After the exposure, the film and the mask are removed, and the exposed layer is developed for 10 seconds in ethanol in an ultrasound bath at 23° C. The drying is carried out at 40° C. for 5 minutes in a fan-assisted oven. The sensitivity of the initiator system used is characterised by the indication of the final wedge step imaged tack-free. The higher the number of steps, the more sensitive the tested system. The results are shown in Table 21.

TABLE 21

| Compound from Ex. | Number of imaged steps after 5s | 10s | 20s | exposure |
|---|---|---|---|---|
| 107 | 11 | 14 | 17 | |
| 108 | 12 | 15 | 18 | |
| 110 | 11 | 13 | 16 | |
| 111 | 10 | 12 | 15 | |
| 112 | 11 | 13 | 16 | |
| 113 | 11 | 13 | 16 | |
| 114 | 13 | 15 | 18 | |
| 120 | 9 | 11 | 13 | |
| 81 | 11 | 14 | 17 | |
| 82B | 8 | 11 | 13 | |
| 83 | 9 | 12 | 14 | |
| 84 | 10 | 13 | 15 | |
| 85 | 11 | 14 | 16 | |
| 87 | 10 | 12 | 15 | |
| 88A | 10 | 12 | 15 | |
| 89 | 11 | 14 | 17 | |
| 90 | 11 | 13 | 16 | |
| 97 | 11 | 13 | 16 | |
| 98 | 10 | 12 | 15 | |
| 101 | 10 | 12 | 15 | |
| 102 | 12 | 15 | 18 | |
| 103 | 10 | 13 | 16 | |
| 99 | 10 | 13 | 16 | |
| 100 | 10 | 13 | 16 | |
| 105 | 10 | 12 | 15 | |
| 106 | 10 | 13 | 16 | |

EXAMPLE 124

Reactivity in a Solder Resist Formulation

A composition is prepared from:
37.64 g of trimethylolpropane triacrylate, Degussa
10.76 g of hexamethoxymethylmelamine ®Cymel 301, American Cyanamid Corp.
47.30 g of polyacrylate containing 3-5% of carboxyl groups ®Carboset 525, B.F. Goodrich, Ohio, USA
4.30 g of polyvinylpyrrolidone PVP 30, GAF AG, Zug, Switzerland.

To 100 g of this composition are added
0.5 g of Irgalith Green
319.0 g of methylene chloride and
30.0 g of methanol.

Portions of this composition are mixed with 0.3%, based on the solids content, of the titanocene compound to be tested. All operations are carried out under a red light. The samples mixed with initiator are applied in a thickness of 200 μm to a 300 μm aluminium foil. The dry layer thickness is 30–35 μm. The sample is allowed to dry at room temperature for 5 minutes. The solvent is then removed by warming at 60° C. for 15 minutes in a fan-assisted oven. A 76 μm thick polyester film is applied to the layer, and a standardised test negative having 21 steps of different optical density (Stauffer wedge) is placed thereon. The sample is covered by a second UV-transparent polyester film and pressed against a metal plate by means of vacuum. The sample is then exposed by means of a 5 kW lamp in a first test series for 10 seconds, in a second test series for 20 seconds and in a third test series for 40 seconds at a distance of 30 cm. After the exposure, the films and the mask are removed, and the exposed layer is developed with developer* for 4 minutes at 23° C. in an ultrasound bath and subsequently dried for 5 minutes at 40° C. The sensitivity of the initiator system used is characterised by the indication of the final wedge step imaged tackfree. The higher the number of steps, the more sensitive the system.

*The developer comprises:
15.00 g of sodium metasilicate.9 $H_2O$
0.16 g of potassium hydroxide
3.00 g of polyethylene glycol 6000
0.50 g of levulinic acid
1000.5 g of demineralised water The results are shown in Table 22.

TABLE 22

| Compound from Ex. | Number of imaged steps after 10s | 20s | 40s | exposure |
|---|---|---|---|---|
| 81 | 12 | 14 | 17 | |
| 82B | 12 | 14 | 17 | |
| 83 | 11 | 14 | 16 | |
| 84 | 11 | 13 | 16 | |
| 85 | 11 | 13 | 16 | |
| 87 | 10 | 12 | 15 | |
| 88A | 10 | 12 | 15 | |
| 89 | 12 | 14 | 17 | |
| 90 | 11 | 13 | 16 | |
| 97 | 12 | 14 | 16 | |
| 98 | 10 | 12 | 15 | |
| 101 | 10 | 12 | 15 | |
| 102 | 13 | 15 | 17 | |
| 103 | 10 | 12 | 15 | |
| 99 | 11 | 13 | 16 | |
| 100 | 11 | 13 | 15 | |
| 105 | 11 | 13 | 16 | |
| 106 | 11 | 13 | 16 | |
| 107 | 12 | 14 | 17 | |
| 108 | 13 | 16 | 19 | |
| 110 | 11 | 13 | 16 | |
| 111 | 11 | 13 | 15 | |
| 112 | 11 | 13 | 16 | |
| 113 | 10 | 12 | 15 | |
| 114 | 15 | 17 | 20 | |
| 120 | 10 | 12 | 15 | |

What is claimed is:

1. A compound of the formula I or II

(I)

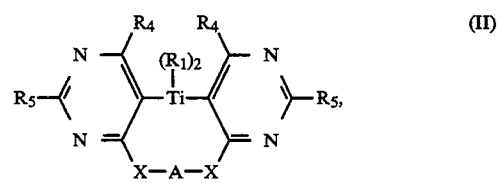
(II)

in which both $R_1$ radicals are, independently of one another, cyclopentadienyl⊖, indenyl⊖ or 4,5,6,7-tetrahydroindenyl⊖, these radicals being unsubstituted or substituted by $C_1$-$C_{18}$alkyl, $C_1$-$C_{18}$alkoxy, $C_2$-$C_{18}$alkenyl, $C_5$-$C_8$cycloalkyl, $C_1$-$C_4$alkyl-$C_5$-$C_8$cycloalkyl, phenyl, naphthyl, phenyl-substituted $C_1$-$C_{12}$alkyl, —Si($R_2$)$_3$, —Ge($R_2$)$_3$, cyano, Cl, Br or I, and the two $R_2$ radicals, independently of one another, are $C_1$-$C_{12}$alkyl, $C_5$-$C_8$cycloalkyl, or unsubstituted or $C_1$-$C_6$alkyl-substituted phenyl or benzyl,

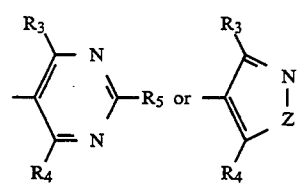

Q is a radical,

Z is $-NR_{10}-$, $-O-$ or $-S-$,

Y is Cl, Br, I, CN, SCN, $-O-CO-CH_3$, $-O-CO-$phenyl or $-O-SO_2-CH_3$, n is 1 or 2, m is 0 or 1, where the sum of n and m must be 2, $R_3$, $R_4$ and $R_5$, independently of one another, are hydrogen, Cl, Br, I, unsubstituted or $C_1-C_4$alkoxy-, $C_5-C_6$cycloalkyl- or phenyl-substituted $C_1-C_{12}$alkyl, unsubstituted or $C_1-C_4$alkyl-substituted $C_3-C_8$cycloalkyl or adamantyl, or $R_3$, $R_4$ and $R_5$ are phenyl, pyrryl, furyl, thienyl, imidazolyl, pyridyl, naphthyl, anthryl, phenanthryl or biphenylyl where the radicals phenyl, pyrryl, furyl, thienyl, imidazolyl, pyridyl, naphthyl, anthryl, phenanthryl or biphenylyl are unsubstituted or substituted by $C_1-C_{12}$alkyl, cyclopentyl, cyclohexyl, Cl, Br, I, $C_1-C_8$alkylthio, $-NR_8R_9$, phenyl, phenylthio or- /and $C_1-C_{10}$alkoxy, or $R_3$, $R_4$ and $R_5$ are unsubstituted $C_2-C_{12}$alkenyl or $C_2-C_{12}$alkenyl which is substituted by unsubstituted or $C_1-C_4$alkyl-, $C_1-C_4$alkoxy-, $C_1-C_4$alkylthio-, Cl-, Br- or I-substituted phenyl or

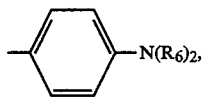

or $R_3$, $R_4$ and $R_5$ are unsubstituted or $C_5-C_8$cycloalkyl- or phenoxy-substituted $C_1-C_{12}$alkoxy, $C_2-C_{12}$alkoxy which is interrupted by one or more oxygen atoms, unsubstituted or $C_1-C_4$alkyl-substituted $C_3-C_{12}$cycloalkoxy, unsubstituted or $C_1-C_4$alkoxy- and/or $C_1-C_4$alkyl-substituted phenoxy, unsubstituted or $C_1-C_4$alkyl-substituted benzyloxy, tetrahydrofurfuryloxy, $C_2-C_6$alkenyloxy, $-O-Si-(R_7)_3$, $C_1-C_8$alkylthio, $C_3-C_8$cycloalkylthio, unsubstituted or $C_1-C_4$alkyl- and/or $C_1-C_4$alkoxy-substituted benzylthio, unsubstituted or $C_1-C_4$alkyl- and/or $C_1-C_4$alkoxy-substituted phenylthio, $-S(O)R_8$, $-SO_2R_8$, $-N(R_9)_2$,

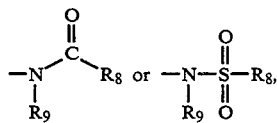

where $R_3$ and $R_4$ are not simultaneously hydrogen, and at least one radical $R_3$ or $R_4$ in the

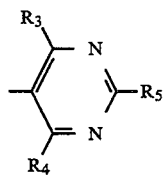

radical is unsubstituted or $C_5-C_8$cycloalkyl- or phenoxy-substituted $C_1-C_{12}$alkoxy, $C_2-C_{12}$alkoxy which is interrupted by one or more oxygen atoms, unsubstituted or $C_1-C_4$alkyl-substituted $C_3-C_{12}$cycloalkoxy, unsubstituted or $C_1-C_4$alkoxy-and/or $C_1-C_4$alkyl-substituted phenoxy, unsubstituted or $C_1-C_4$alkyl-substituted benzyloxy, tetrahydrofur-furyloxy or $C_2-C_6$alkenyloxy, and in the case where Z is $-NR_{10}-$, $R_3$ and $R_4$ are Cl, Br or I, the two $R_6$ radicals, independently of one another, are $C_1-C_4$alkyl or $C_2-C_{10}$alkenyl, or the two $R_6$ radicals, together with the nitrogen atom to which they are bonded, form a morpholino radical, $R_7$ is $C_1-C_{12}$alkyl, $C_5-C_8$cycloalkyl or unsubstituted or $C_1-C_6$alkyl-substituted phenyl, $R_8$ is unsubstituted or $C_1-C_4$alkyl-substituted phenyl or $\alpha$-tertiary $C_4-C_6$alkyl, $R_9$ is unsubstituted or phenyl-, $C_7-C_{12}$alkylphenyl-, $C_5-C_8$cycloalkyl- or $C_1-C_4$alkyl-$C_5-C_8$cycloalkyl-substituted $C_1-C_8$alkyl, $C_2-C_8$alkenyl, unsubstituted or $C_1-C_4$alkyl-substituted $C_5-C_8$cycloalkyl, $C_6-C_{20}$cycloalkenylalkyl, unsubstituted or $C_1-C_{12}$alkyl-substituted phenyl,

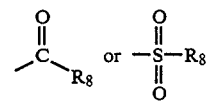

radical, where, in addition, the two $R_9$ radicals in $-N(R_9)_2$ are identical or different and, together with the nitrogen atom to which they are bonded, may form a 5- or 6-membered heterocyclic ring which, in addition to the nitrogen atom, may also contain further nitrogen, oxygen or sulfur atoms, or the two $R_9$ radicals, together with the nitrogen atom to which they are bonded, form a

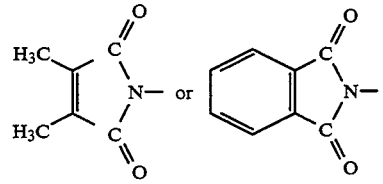

radical, $R_{10}$ is as defined for $R_9$ or additionally is naphthyl, biphenylyl, pyridyl or pyrimidinyl, these radicals being unsubstituted or substituted by Cl, Br, I, $NO_2$, $C_1-C_{12}$alkyl, $C_1-C_{10}$alkoxy, $C_1-C_8$alkylthio, phenylthio, morpholino or $-N(C_1-C_4$alkyl$)_2$, or $R_{10}$ is phenyl which is substituted by Cl, Br, I, $NO_2$, $C_1-C_{10}$alkoxy, $C_1-C_8$alkylthio, phenylthio, morpholino or $-N(C_1-C_4$alkyl$)_2$, X is $-O-$, $-S-$,

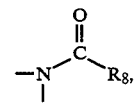

methylene or ethylene, and

A is $C_1-C_{12}$alkylene or $-X-A-X-$ is a direct bond.

2. A compound according to claim 1, in which the two $R_1$ radicals, independently of one another, are cyclopentadienyl$^\ominus$ which is unsubstituted or substituted by $C_1-C_{18}$alkyl, $C_1-C_{18}$alkoxy, $C_2-C_{18}$alkenyl, $-Si(R_2)_3$ or Cl, Br,I.

3. A compound of the formula I according to claim 1, in which $R_3$ and $R_5$ are unsubstituted or $C_5-C_8$cycloalkyl- or phenoxy-substituted $C_1-C_{12}$alkoxy, $C_2-C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy.

4. A compound according to claim 1, in which $R_5$ is $C_1$-$C_8$alkylthio, $C_3$-$C_8$cycloalkylthio, unsubstituted or $C_1$-$C_4$alkyl- and/or $C_1$-$C_4$alkoxy-substituted benzylthio, unsubstituted or $C_1$-$C_4$alkyl- and/or $C_1$-$C_4$alkoxy-substituted phenylthio, —S(O)$R_8$ or —SO$_2R_8$.

5. A compound of the formula I according to claim 1, in which Q is a

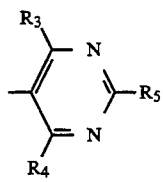

radical.

6. A compound according to claim 5, in which $R_5$ is phenyl, pyrryl, furyl, thienyl, imidazolyl, pyridyl, naphthyl, anthryl, phenanthryl or biphenylyl, where the radicals phenyl, pyrryl, furyl, thienyl, imidazolyl, pyridyl, naphthyl, anthryl, phenanthryl and biphenylyl are unsubstituted or substituted by alkyl, $C_1$-$C_{12}$cyclopentyl, cyclohexyl, Cl, Br, I, $C_1$-$C_8$alkylthio, —NR$_8$R$_9$, phenyl, phenylthio or $C_1$-$C_{10}$alkoxy.

7. A compound of the formula I according to claim 1, in which $R_3$, $R_4$ and $R_5$, independently of one another, are unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy.

8. A compound according to claim 1, in which $R_4$ is Cl, Br or I.

9. A compound of the formula I according to claim 1, in which $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy, $R_4$ is Cl, and $R_5$ is phenyl which is unsubstituted or substituted by $C_1$-$C_{12}$alkyl, Cl, Br, $C_1$-$C_8$alkylthio, —NR$_8$R$_9$, phenyl, phenylthio or $C_1$-$C_{10}$alkoxy.

10. A compound of the formula I according to claim 1, in which $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, unsubstituted or $C_1$-$C_4$alkyl-substituted $C_3$-$C_{12}$cycloalkoxy, unsubstituted or $C_1$-$C_4$alkoxy- and/or $C_1$-$C_4$alkyl-substituted phenoxy, unsubstituted or $C_1$-$C_4$alkyl-substituted benzyloxy, tetrahydrofurfuryloxy or $C_2$-$C_6$alkenyloxy, $R_4$ is Cl, and $R_5$ is $C_1$-$C_{12}$alkyl, $C_3$-$C_8$cycloalkyl or adamantyl.

11. A compound of the formula I according to claim 1, in which n=2 and m=0.

12. A compound according to claim 1, in which Y is Cl, Br or I.

13. A compound of the formula I according to claim 1, in which Y is Cl, —O—CO—CH$_3$ or —O—CO—phenyl, $R_3$ is unsubstituted or $C_5$-$C_8$cycloalkyl- or phenoxy-substituted $C_1$-$C_{12}$alkoxy, $C_2$-$C_{12}$alkoxy which is interrupted by one or more oxygen atoms, $C_5$-$C_8$cycloalkoxy, benzyloxy, tetrahydrofurfuryloxy or Cl, $R_4$ is as defined for $R_3$ or additionally hydrogen, and $R_5$ is as defined for $R_3$ or additionally hydrogen, $C_1$-$C_{12}$alkyl, $C_1$-$C_8$alkylthio, pyrryl, or phenyl which is unsubstituted or substituted by cl, $C_1$-$C_{10}$alkoxy, phenyl, $C_1$-$C_8$alkylthio, phenylthio or —NR$_8$R$_9$, and $R_{10}$ is phenyl.

14. A compound of the formula I according to claim 1, in which Q is a

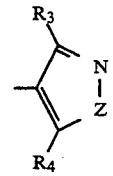

radical.

15. A compound according to claim 14, in which $R_3$ and $R_4$ are Cl,

Z is —NR$_{10}$—, and $R_{10}$ is phenyl which is unsubstituted or substituted by Cl, Br, I, NO$_2$, $C_1$-$C_{12}$alkyl, $C_1$-$C_{10}$alkoxy, $C_1$-$C_8$alkylthio, phenylthio, morpholino or —N($C_1$-$C_4$alkyl)$_2$.

16. A photopolymerisable composition comprising
  (a) at least one ethylenically unsaturated, photopolymerisable compound and
  (b), as photoinitiator, at least one compound of the formula I or II as defined in claim 1.

17. A composition according to claim 16, which, in addition to the photoinitiator (b), also contains at least one further photoinitiator (c) and/or other additives.

18. A composition according to claim 16, containing from 0.05 to 15% by weight of component (b), based on the composition.

19. A method for the production of paints, printing inks, printing plates, dental compositions, resist materials and image-recording materials, which comprises incorporating into or applying to said materials a composition according to claim 16.

20. A coated substrate which is coated on at least one surface with a composition according to claim 16.

21. A process for the photographic production of relief images, wherein a coated substrate according to claim 20 is exposed imagewise, and the unexposed areas are then removed by means of a solvent.

22. A process for the photopolymerisation of non-volatile, monomeric, oligomeric or polymeric compounds containing at least one ethylenically unsaturated double bond, wherein a compound of the formula I or II according to claim 1 is added to the abovementioned compounds and the mixture is irradiated with light in the range from 200 to 600 nm.

23. A compound of the formula I

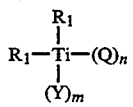

in which both $R_1$ radicals are, independently of one another, cyclopentadienyl$^\ominus$, , indenyl$^\ominus$ or 4,5,6,7-tetrahydroindenyl$^\ominus$, these radicals being unsubstituted or substituted by $C_1$–$C_{18}$alkyl, $C_1$–$C_{18}$alkoxy, $C_2$–$C_{18}$alkenyl, $C_5$–$C_8$cycloalkyl, $C_1$–$C_4$alkyl-$C_5$–$C_8$cycloalkyl, phenyl, naphthyl, phenyl-substituted $C_1$–$C_{12}$alkyl, —Si$(R_2)_3$, —Ge$(R_2)_3$, cyano, Cl, Br or I, and the two $R_2$ radicals, independently of one another, are $C_1$–$C_{12}$alkyl, $C_5$–$C_8$cycloalkyl, or unsubstituted or $C_1$–$C_6$alkyl-substituted phenyl or benzyl,

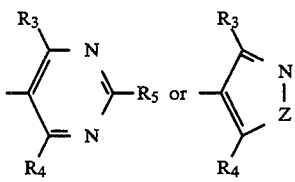

radical,
Z is —$NR_{10}$—, —O— or —S—,
Y is Cl, Br, I, CN, SCN or —O—$SO_2$—$CH_3$,
n is 1 or 2,
m is 0 or 1, where the sum of n and m must be 2,
$R_3$, $R_4$ and $R_5$, independently of one another, are hydrogen, Cl, Br, I, unsubstituted or $C_1$–$C_4$alkoxy- or phenyl-substituted $C_1$–$C_{12}$alkyl, unsubstituted or $C_1$–$C_4$alkyl-substituted $C_3$–$C_8$cycloalkyl, unsubstituted or $C_1$–$C_{12}$alkyl-, Cl-, Br-, I-, $C_1$–$C_8$alkylthio-, —$NR_8R_9$— or $C_1$–$C_{10}$alkoxy-substituted phenyl, pyrryl, furyl, thienyl, imidazolyl or pyridyl, or $R_3$, $R_4$ and $R_5$ are unsubstituted $C_2$–$C_{12}$alkenyl or $C_2$–$C_{12}$alkenyl which is substituted by unsubstituted or $C_1$–$C_4$alkyl-, $C_1$–$C_4$alkoxy-, $C_1$–$C_4$alkylthio, Cl-, Br- or I-substituted phenyl or

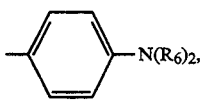

or $R_3$, $R_4$ and $R_5$ are unsubstituted or $C_5$–$C_8$cycloalkyl-substituted $C_1$–$C_{12}$alkoxy, $C_2$–$C_{12}$alkoxy which is interrupted by one or more oxygen atoms, unsubstituted or $C_1$–$C_4$alkyl-substituted $C_3$–$C_{12}$cycloalkoxy, unsubstituted or $C_1$–$C_4$alkoxy- or $C_1$–$C_4$alkyl-substituted phenoxy, unsubstituted or $C_1$–$C_4$alkyl-substituted benzyloxy, tetrahydrofurfuryloxy, $C_2$–$C_6$alkenyloxy, —O—Si—$(R_7)_3$, $C_1$–$C_8$alkylthio, $C_3$–$C_8$cycloalkylthio, unsubstituted or $C_1$–$C_4$alkyl- and/or $C_1$–$C_4$alkoxy-substituted benzylthio, unsubstituted or $C_1$–$C_4$alkyl- and/or $C_1$–$C_4$alkoxy-substituted thiophenyl, —S(O)$R_8$, —$SO_2R_8$, —$N(R_9)_2$,

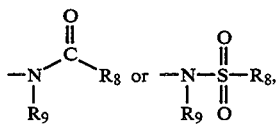

where $R_3$ and $R_4$ are not simultaneously hydrogen, and at least one radical $R_3$ or $R_4$ in the

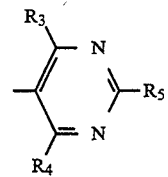

radical is unsubstituted or $C_5$–$C_8$cycloalkyl-substituted $C_1$–$C_{12}$alkoxy, $C_2$–$C_{12}$alkoxy which is interrupted by one or more oxygen atoms, unsubstituted or $C_1$–$C_4$alkyl-substituted $C_3$–$C_{12}$cycloalkoxy, unsubstituted or $C_1$–$C_4$alkoxy- or $C_1$–$C_4$alkyl-substituted phenoxy, unsubstituted or $C_1$–$C_4$alkyl-substituted benzyloxy, tetrahydrofurfuryloxy or $C_2$–$C_6$alkenyloxy, and in the case where Z is —$NR_{10}$—, $R_3$ and $R_4$ are Cl, Br or I, the two $R_6$ radicals, independently of one another, are $C_1$–$C_4$alkyl or $C_2$–$C_{10}$alkenyl, or the two $R_6$ radicals, together with the nitrogen atom to which they are bonded, form a morpholino radical, $R_7$ is $C_1$–$C_{12}$alkyl, $C_5$–$C_8$cycloalkyl or unsubstituted or $C_1$–$C_6$alkyl-substituted phenyl, $R_8$ is unsubstituted or $C_1$–$C_4$alkyl-substituted phenyl or α-tertiary $C_4$–$C_6$alkyl, $R_9$ is unsubstituted or phenyl-, $C_7$–$C_{12}$alkylphenyl-, $C_5$–$C_8$cycloalkyl- or $C_1$–$C_4$alkyl-$C_5$–$C_8$cycloalkyl-substituted $C_1$–$C_8$alkyl, $C_2$–$C_8$alkenyl, unsubstituted or $C_1$–$C_4$alkyl-substituted $C_5$–$C_8$cycloalkyl, $C_6$–$C_{20}$cycloalkenylalkyl, unsubstituted or $C_1$–$C_{12}$alkyl-substituted phenyl, a

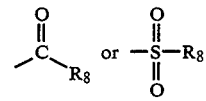

radical, where, in addition, the two $R_9$ radicals in —$N(R_9)_2$ are identical or different and, together with the nitrogen atom to which they are bonded, may form a 5- or 6-membered heterocyclic ring which, in addition to the nitrogen atom, may also contain further nitrogen, oxygen or sulfur atoms, or, if the two $R_9$ radicals are a

group, the two $R_9$ radicals, together with the nitrogen atom to which they are bonded, form a

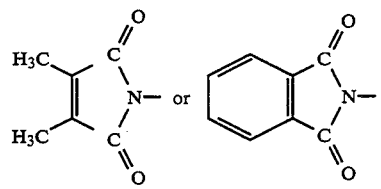

radical,
$R_{10}$ is as defined for $R_9$, and if n=2, the formula I also includes compounds of the formula II
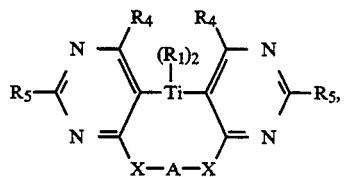
in which
X is —O—, —S—,
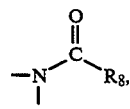
methylene or ethylene, and
A is $C_1$-$C_{12}$alkylene or —X—A—X— is a direct bond.
* * * * *